(12) United States Patent
Miles et al.

(10) Patent No.: US 8,403,841 B2
(45) Date of Patent: *Mar. 26, 2013

(54) SURGICAL ACCESS SYSTEM AND RELATED METHODS

(75) Inventors: Patrick Miles, San Diego, CA (US);
Scot Martinelli, San Diego, CA (US);
Eric Finley, San Diego, CA (US);
James Gharib, San Diego, CA (US);
Allen Farquhar, San Diego, CA (US);
Norbert Kaula, Arvada, CO (US);
Jeffrey Blewett, San Diego, CA (US);
Goretti Medeiros, legal representative, Plantsville, CT (US)

(73) Assignee: NuVasive, Inc., San Diego, CA (US)

( * ) Notice: Subject to any disclaimer, the term of this patent is extended or adjusted under 35 U.S.C. 154(b) by 30 days.

This patent is subject to a terminal disclaimer.

(21) Appl. No.: 12/636,860

(22) Filed: Dec. 14, 2009

(65) Prior Publication Data
US 2010/0160738 A1 Jun. 24, 2010

Related U.S. Application Data

(63) Continuation of application No. 10/759,811, filed on Jan. 16, 2004, now Pat. No. 7,691,057.

(60) Provisional application No. 60/440,905, filed on Jan. 16, 2003.

(51) Int. Cl.
*A61B 1/32* (2006.01)

(52) U.S. Cl. .......................................... 600/214; 60/224

(58) Field of Classification Search .......... 600/184–241; 606/129, 190, 191, 198
See application file for complete search history.

(56) References Cited

U.S. PATENT DOCUMENTS

| 208,227 A | 9/1878 | Dorr |
| 972,983 A | 10/1910 | Arthur |
| 1,328,624 A | 1/1920 | Graham |
| 1,548,184 A | 8/1925 | Cameron |
| 2,704,064 A | 6/1955 | Fizzell et al. |
| 2,736,002 A | 2/1956 | Oriel |
| 2,808,826 A | 10/1957 | Reiner et al. |
| 3,364,929 A | 1/1968 | Ide et al. |
| 3,664,329 A | 5/1972 | Naylor |
| 3,682,162 A | 8/1972 | Colyer |
| 3,785,368 A | 1/1974 | McCarthy et al. |
| 3,830,226 A | 8/1974 | Staub et al. |
| 3,957,036 A | 5/1976 | Normann |
| 4,099,519 A | 7/1978 | Warren |

(Continued)

FOREIGN PATENT DOCUMENTS

| DE | 299 08 259 | 7/1999 |
| EP | 0 972 538 | 1/2000 |

(Continued)

OTHER PUBLICATIONS

Mayer and Brock, "Percutaneous endoscopic discectomy: surgical technique and preliminary results compared to microsurgical discectomy," *J. Neurosurg*, 1993, 78: 216-225.

(Continued)

*Primary Examiner* — Yogesh Patel

(74) *Attorney, Agent, or Firm* — Fish & Richardson P.C.

(57) ABSTRACT

A surgical access system including a tissue distraction assembly and a tissue refraction assembly, both of which may be equipped with one or more electrodes for use in detecting the existence of (and optionally the distance and/or direction to) neural structures before, during, and after the establishment of an operative corridor to a surgical target site.

33 Claims, 18 Drawing Sheets

U.S. PATENT DOCUMENTS

| | | | |
|---|---|---|---|
| 4,164,214 A | 8/1979 | Stark et al. | |
| 4,207,897 A | 6/1980 | Lloyd et al. | |
| 4,224,949 A | 9/1980 | Scott et al. | |
| 4,226,228 A | 10/1980 | Shin et al. | |
| 4,235,242 A | 11/1980 | Howson et al. | |
| 4,285,347 A | 8/1981 | Hess | |
| 4,291,705 A | 9/1981 | Severinghaus et al. | |
| 4,461,300 A | 7/1984 | Christensen | |
| 4,515,168 A | 5/1985 | Chester et al. | |
| 4,519,403 A | 5/1985 | Dickhudt | |
| 4,545,374 A | 10/1985 | Jacobson | |
| 4,561,445 A | 12/1985 | Berke et al. | |
| 4,562,832 A | 1/1986 | Wilder et al. | |
| 4,573,448 A | 3/1986 | Kambin | |
| 4,592,369 A | 6/1986 | Davis et al. | |
| 4,595,018 A | 6/1986 | Rantala | |
| 4,611,597 A | 9/1986 | Kraus | |
| 4,633,889 A | 1/1987 | Talalla | |
| 4,658,835 A | 4/1987 | Pohndorf | |
| 4,744,371 A | 5/1988 | Harris | |
| 4,759,377 A | 7/1988 | Dykstra | |
| 4,784,150 A | 11/1988 | Voorhies et al. | |
| 4,807,642 A | 2/1989 | Brown | |
| 4,892,105 A | 1/1990 | Prass | |
| 4,913,134 A | 4/1990 | Luque | |
| 4,926,865 A | 5/1990 | Oman | |
| 4,962,766 A | 10/1990 | Herzon | |
| 4,964,411 A | 10/1990 | Johnson et al. | |
| 5,007,902 A | 4/1991 | Witt | |
| 5,052,373 A | 10/1991 | Michelson | |
| 5,058,602 A | 10/1991 | Brody | |
| 5,081,990 A | 1/1992 | Deletis | |
| 5,092,344 A | 3/1992 | Lee | |
| 5,127,403 A | 7/1992 | Brownlee | |
| 5,161,533 A | 11/1992 | Prass et al. | |
| 5,171,279 A | 12/1992 | Mathews | |
| 5,195,541 A | 3/1993 | Obenchain | |
| 5,196,015 A | 3/1993 | Neubardt | |
| RE34,390 E | 9/1993 | Culver | |
| 5,255,691 A | 10/1993 | Otten | |
| 5,282,468 A | 2/1994 | Klepinski | |
| 5,284,153 A | 2/1994 | Raymond et al. | |
| 5,284,154 A | 2/1994 | Raymond et al. | |
| 5,295,994 A | 3/1994 | Bonutti | |
| 5,299,563 A | 4/1994 | Seton | |
| 5,312,417 A | 5/1994 | Wilk | |
| 5,313,956 A | 5/1994 | Knutsson et al. | |
| 5,313,962 A | 5/1994 | Obenchain | |
| 5,327,902 A | 7/1994 | Lemmen | |
| 5,331,975 A | 7/1994 | Bonutti | |
| 5,333,618 A | 8/1994 | Lekhtman et al. | |
| 5,342,384 A | 8/1994 | Sugarbaker | |
| 5,375,067 A | 12/1994 | Berchin | |
| 5,375,594 A | 12/1994 | Cueva | |
| 5,383,876 A | 1/1995 | Nardella | |
| 5,395,317 A | 3/1995 | Kambin | |
| 5,450,845 A | 9/1995 | Alexgaard | |
| 5,474,057 A | 12/1995 | Makower et al. | |
| 5,474,558 A | 12/1995 | Neubardt | |
| 5,480,440 A | 1/1996 | Kambin | |
| 5,482,038 A | 1/1996 | Ruff | |
| 5,484,437 A | 1/1996 | Michelson | |
| 5,509,893 A | 4/1996 | Pracas | |
| 5,514,153 A | 5/1996 | Bonutti | |
| 5,540,235 A | 7/1996 | Wilson | |
| 5,549,656 A | 8/1996 | Reiss | |
| 5,560,372 A | 10/1996 | Cory | |
| 5,566,678 A | 10/1996 | Cadwell | |
| 5,571,149 A | 11/1996 | Liss et al. | |
| 5,579,781 A | 12/1996 | Cooke | |
| 5,593,429 A | 1/1997 | Ruff | |
| 5,599,279 A | 2/1997 | Slotman et al. | |
| 5,630,813 A | 5/1997 | Kieturakis | |
| 5,667,508 A | 9/1997 | Errico et al. | |
| 5,671,752 A | 9/1997 | Sinderby et al. | |
| 5,681,265 A | 10/1997 | Maeda et al. | |
| 5,707,359 A | 1/1998 | Bufalini | |
| 5,711,307 A | 1/1998 | Smits | |
| 5,728,046 A | 3/1998 | Mayer et al. | |
| 5,741,253 A | 4/1998 | Michelson | |
| 5,759,159 A | 6/1998 | Masreliez | |
| 5,762,629 A | 6/1998 | Kambin | |
| 5,772,661 A | 6/1998 | Michelson | |
| 5,775,331 A | 7/1998 | Raymond et al. | |
| 5,776,144 A | 7/1998 | Leysieffer et al. | |
| 5,779,642 A | 7/1998 | Nightengale | |
| 5,785,658 A | 7/1998 | Benaron | |
| 5,792,044 A | 8/1998 | Foley et al. | |
| 5,797,854 A | 8/1998 | Hedgecock | |
| 5,814,073 A | 9/1998 | Bonutti | |
| 5,830,151 A | 11/1998 | Hadzic et al. | |
| 5,851,191 A | 12/1998 | Gozani | |
| 5,853,373 A | 12/1998 | Griffith et al. | |
| 5,860,973 A | 1/1999 | Michelson | |
| 5,862,314 A | 1/1999 | Jeddeloh | |
| 5,872,314 A | 2/1999 | Clinton | |
| 5,885,210 A | 3/1999 | Cox | |
| 5,885,219 A | 3/1999 | Nightengale | |
| 5,888,196 A | 3/1999 | Bonutti | |
| 5,891,147 A | 4/1999 | Moskovitz et al. | |
| 5,902,231 A | 5/1999 | Foley et al. | |
| 5,928,139 A * | 7/1999 | Koros et al. | 600/205 |
| 5,928,158 A | 7/1999 | Aristides | |
| 5,931,777 A * | 8/1999 | Sava | 600/213 |
| 5,935,131 A | 8/1999 | Bonutti et al. | |
| 5,938,688 A | 8/1999 | Schiff | |
| 5,944,658 A | 8/1999 | Koros et al. | |
| 5,976,094 A | 11/1999 | Gozani et al. | |
| 6,004,262 A | 12/1999 | Putz et al. | |
| 6,004,312 A | 12/1999 | Finneran | |
| 6,007,487 A | 12/1999 | Foley et al. | |
| 6,024,696 A | 2/2000 | Hoftman et al. | |
| 6,027,456 A | 2/2000 | Feler et al. | |
| 6,038,469 A | 3/2000 | Karlsson et al. | |
| 6,038,477 A | 3/2000 | Kayyali | |
| 6,050,992 A | 4/2000 | Nichols | |
| 6,074,343 A | 6/2000 | Nathanson et al. | |
| 6,083,154 A | 7/2000 | Liu et al. | |
| 6,095,987 A | 8/2000 | Schmulewitz | |
| 6,104,957 A | 8/2000 | Alo et al. | |
| 6,104,960 A | 8/2000 | Duysens et al. | |
| 6,120,503 A | 9/2000 | Michelson | |
| 6,126,660 A | 10/2000 | Dietz | |
| 6,132,386 A | 10/2000 | Gozani et al. | |
| 6,132,387 A | 10/2000 | Gozani et al. | |
| 6,135,965 A | 10/2000 | Tumer et al. | |
| 6,139,493 A | 10/2000 | Koros et al. | |
| 6,146,335 A | 11/2000 | Gozani | |
| 6,152,871 A | 11/2000 | Foley et al. | |
| 6,161,047 A | 12/2000 | King et al. | |
| 6,174,311 B1 | 1/2001 | Branch et al. | |
| 6,181,961 B1 | 1/2001 | Prass | |
| 6,196,969 B1 | 3/2001 | Bester et al. | |
| 6,206,826 B1 | 3/2001 | Mathews et al. | |
| 6,217,509 B1 | 4/2001 | Foley et al. | |
| 6,224,549 B1 | 5/2001 | Drongelen | |
| 6,259,945 B1 | 7/2001 | Epstein et al. | |
| 6,264,651 B1 | 7/2001 | Underwood et al. | |
| 6,266,558 B1 | 7/2001 | Gozani et al. | |
| 6,273,905 B1 | 8/2001 | Streeter | |
| 6,292,701 B1 | 9/2001 | Prass et al. | |
| 6,306,100 B1 | 10/2001 | Prass | |
| 6,308,712 B1 | 10/2001 | Shaw | |
| 6,312,392 B1 | 11/2001 | Herzon | |
| 6,325,764 B1 | 12/2001 | Griffith et al. | |
| 6,334,068 B1 | 12/2001 | Hacker | |
| 6,348,058 B1 | 2/2002 | Melkent et al. | |
| 6,360,750 B1 | 3/2002 | Gerber et al. | |
| 6,371,968 B1 * | 4/2002 | Kogasaka et al. | 606/190 |
| 6,425,859 B1 * | 7/2002 | Foley et al. | 600/204 |
| 6,425,901 B1 | 7/2002 | Zhu et al. | |
| 6,450,952 B1 | 9/2002 | Rioux et al. | |
| 6,451,015 B1 | 9/2002 | Rittman, III et al. | |
| 6,466,817 B1 | 10/2002 | Kaula et al. | |
| 6,468,205 B1 | 10/2002 | Mollenauer et al. | |
| 6,468,207 B1 | 10/2002 | Fowler, Jr. | |
| 6,500,128 B2 | 12/2002 | Marino | |

| | | |
|---|---|---|
| 6,520,907 B1 | 2/2003 | Foley et al. |
| 6,524,320 B2 | 2/2003 | DiPoto |
| 6,535,759 B1 | 3/2003 | Epstein et al. |
| 6,564,078 B1 | 5/2003 | Marino et al. |
| 6,579,244 B2 | 6/2003 | Goodwin |
| 6,620,157 B1 | 9/2003 | Dabney et al. |
| 6,645,194 B2 | 11/2003 | Briscoe et al. |
| 6,679,833 B2 | 1/2004 | Smith et al. |
| 6,719,692 B2 | 4/2004 | Kleffner et al. |
| 6,760,616 B2 | 7/2004 | Hoey et al. |
| 6,770,074 B2 | 8/2004 | Michelson |
| 6,796,985 B2 | 9/2004 | Bolger et al. |
| 6,810,281 B2 | 10/2004 | Brock et al. |
| 6,819,956 B2 | 11/2004 | DiLorenzo |
| 6,847,849 B2 | 1/2005 | Mamo et al. |
| 6,849,047 B2 | 2/2005 | Goodwin |
| 6,855,105 B2 | 2/2005 | Jackson, III et al. |
| 6,871,099 B1 | 3/2005 | Whitehurst et al. |
| 6,902,569 B2 | 6/2005 | Parmer et al. |
| 6,926,728 B2 | 8/2005 | Zucherman et al. |
| 6,929,606 B2 | 8/2005 | Ritland |
| 6,945,933 B2 * | 9/2005 | Branch et al. ............... 600/210 |
| 6,951,538 B2 | 10/2005 | Ritland |
| 7,047,082 B1 | 5/2006 | Schrom et al. |
| 7,050,848 B2 | 5/2006 | Hoey et al. |
| 7,079,883 B2 | 7/2006 | Marino et al. |
| 7,089,059 B1 | 8/2006 | Pless |
| 7,177,677 B2 | 2/2007 | Kaula et al. |
| 7,198,598 B2 | 4/2007 | Smith et al. |
| 7,207,949 B2 | 4/2007 | Miles et al. |
| 7,226,451 B2 | 6/2007 | Shluzas et al. |
| 7,261,688 B2 | 8/2007 | Smith et al. |
| 7,470,236 B1 | 12/2008 | Kelleher et al. |
| 7,473,222 B2 | 1/2009 | Dewey et al. |
| 7,481,766 B2 | 1/2009 | Lee et al. |
| 7,522,953 B2 | 4/2009 | Kaula et al. |
| 7,556,601 B2 | 7/2009 | Branch et al. |
| 7,582,058 B1 | 9/2009 | Miles et al. |
| 7,643,884 B2 | 1/2010 | Pond et al. |
| 7,691,057 B2 | 4/2010 | Miles et al. |
| 7,819,801 B2 | 10/2010 | Miles et al. |
| 7,935,051 B2 | 5/2011 | Miles et al. |
| 2001/0039949 A1 | 11/2001 | Loubser |
| 2001/0056280 A1 | 12/2001 | Underwood et al. |
| 2002/0007129 A1 | 1/2002 | Marino |
| 2002/0010392 A1 | 1/2002 | Desai |
| 2002/0072686 A1 | 6/2002 | Hoey et al. |
| 2002/0077632 A1 | 6/2002 | Tsou |
| 2002/0123780 A1 | 9/2002 | Grill et al. |
| 2002/0161415 A1 | 10/2002 | Cohen et al. |
| 2002/0193843 A1 | 12/2002 | Hill et al. |
| 2003/0032966 A1 | 2/2003 | Foley et al. |
| 2003/0105503 A1 | 6/2003 | Marino |
| 2003/0139648 A1 | 7/2003 | Foley et al. |
| 2003/0149341 A1 | 8/2003 | Clifton |
| 2003/0225405 A1 | 12/2003 | Weiner |
| 2003/0236544 A1 | 12/2003 | Lunsford et al. |
| 2004/0133077 A1 * | 7/2004 | Obenchain et al. ............ 600/224 |
| 2004/0199084 A1 | 10/2004 | Kelleher et al. |
| 2004/0225228 A1 | 11/2004 | Ferree |
| 2005/0004593 A1 | 1/2005 | Simonson |
| 2005/0004623 A1 | 1/2005 | Miles et al. |
| 2005/0033380 A1 | 2/2005 | Tanner et al. |
| 2005/0075578 A1 | 4/2005 | Gharib et al. |
| 2005/0080320 A1 | 4/2005 | Lee et al. |
| 2005/0149035 A1 | 7/2005 | Pimenta et al. |
| 2005/0182454 A1 | 8/2005 | Gharib et al. |
| 2005/0192575 A1 | 9/2005 | Pacheco |
| 2006/0025703 A1 | 2/2006 | Miles et al. |
| 2006/0052828 A1 | 3/2006 | Kim et al. |
| 2006/0069315 A1 | 3/2006 | Miles et al. |
| 2006/0224078 A1 | 10/2006 | Hoey et al. |
| 2007/0016097 A1 | 1/2007 | Farquhar et al. |
| 2007/0198062 A1 | 8/2007 | Miles et al. |
| 2007/0293782 A1 | 12/2007 | Marino |
| 2008/0058606 A1 | 3/2008 | Miles et al. |
| 2008/0064976 A1 | 3/2008 | Kelleher et al. |
| 2008/0064977 A1 | 3/2008 | Kelleher et al. |
| 2008/0065178 A1 | 3/2008 | Kelleher et al. |
| 2008/0071191 A1 | 3/2008 | Kelleher et al. |
| 2008/0097164 A1 | 4/2008 | Miles et al. |
| 2008/0300465 A1 | 12/2008 | Feigenwinter et al. |
| 2009/0124860 A1 | 5/2009 | Miles et al. |
| 2009/0138050 A1 | 5/2009 | Ferree |
| 2009/0192403 A1 | 7/2009 | Gharib et al. |
| 2009/0204016 A1 | 8/2009 | Gharib et al. |
| 2010/0069783 A1 | 3/2010 | Miles et al. |
| 2010/0130827 A1 | 5/2010 | Pimenta et al. |
| 2010/0152603 A1 | 6/2010 | Miles et al. |
| 2010/0160738 A1 | 6/2010 | Miles et al. |
| 2010/0174148 A1 | 7/2010 | Miles et al. |

FOREIGN PATENT DOCUMENTS

| | | |
|---|---|---|
| FR | 2 795 624 | 1/2001 |
| WO | WO 00/38574 | 7/2000 |
| WO | WO 00/66217 | 11/2000 |
| WO | WO 00/67645 | 11/2000 |
| WO | WO 01/37728 | 5/2001 |
| WO | WO 02/054960 | 7/2002 |
| WO | WO 03/005887 | 1/2003 |
| WO | WO 03/026482 | 4/2003 |
| WO | WO 03/037170 | 5/2003 |
| WO | WO 2005/013805 | 2/2005 |
| WO | WO 2005/030318 | 4/2005 |
| WO | WO 2006/042241 | 4/2006 |
| WO | WO 2006/066217 | 6/2006 |

OTHER PUBLICATIONS

Schaffer and Kambin, "Percutaneous Posterolateral Lumbar Discectomy and Decompression with a 6.9-Millimeter Cannula," *The Journal of Bone and Joint Surgery*, 1991, 73A(6): 822-831.

Friedman, "Percutaneous discectomy: An alternative to chemonucleolysis," *Neurosurgery*, 1983, 13(5): 542-547.

Bergey et al., "Endoscopic Lateral Transpsoas Approach to the Lumbar Spine," *Spine*, 2004, 29(15): 1681-1688.

Dezawa et al., "Retroperitoneal Laparoscopic Lateral Approach to the Lumbar Spine: A New Approach, Technique, and Clinical Trial," *Journal of Spinal Disorders*, 2000, 13(2): 138-143.

Gardocki, "Tubular diskectomy minimizes collateral damage: A logical progression moves spine surgery forward," *AAOS Now*, 2009, 5 pages.

Hovorka et al., "Five years' experience of retroperitoneal lumbar and thoracolumbar surgery," *Eur Spine J.*, 2000, 9(1): S30-S34.

Kossman et al., "The use of a retractor system (SynFrame) for open, minimal invasive reconstruction of the anterior column of the thoracic and lumbar spine," *Eur Spine J.*, 2001, 10: 396-402.

Mayer, "A New Microsurgical Technique for Minimally Invasive Anterior Lumbar Interbody Fusion," *Spine*, 1997, 22(6): 691-699.

Mayer, "The ALIF Concept," *Eur Spine J.*, 2000, 9(1): S35-S43.

Mayer and Wiechert, "Microsurgical Anterior Approaches to the Lumbar Spine for Interbody Fusion and Total Disc Replacement," *Neurosurgery*, 2002, 51(2): 159-165.

McAfee et al., "Minimally Invasive Anterior Retroperitoneal Approach to the Lumbar Spine: Emphasis on the Lateral BAK," *Spine, 1998*, 23(13): 1476-1484.

Rao, et al. "Dynamic retraction of the psoas muscle to expose the lumbar spine using the retroperitoneal approach," *J. Neurosurg Spine*, 2006, 5: 468-470.

Wolfla et al., "Retroperitoneal lateral lumbar interbody fusion with titanium threaded fusion cages," *J. Neurosurg (Spine 1)*, 2002, 96: 50-55.

Crock, H.V. MD., "Anterior Lumbar Interbody Fusion," Clinical Orthopaedics and Related Research, Number One Hundred Sixty Five, 1982, pp. 157-163, 13 pages.

Larson and Maiman, "Surgery of the Lumbar Spine," Thieme Medical Publishers, Inc., 1999, pp. 305-319.

Medtronic XOMED Surgical Products, Inc., NIM-Response Nerve Integrity Monitor Intraoperative EMG Monitor User's Guide, Revision B, 2000, 47 pages.

"NuVasive's spine surgery system cleared in the US," Pharm & Medical Industry Week, Dec. 10, 2001, 1 page.

Pimenta, "Initial Clinical Results of Direct Lateral, Minimally Invasive Access to the Lumbar Spine for Disc Nucleus Replacement Using a Novel Neurophysiological Monitoring System." *The 9th IMAST*, May, 2002, 1 page.
Pimenta et al., "The Lateral Endoscopic Transpsoas Retroperitoneal Approach (Letra) for Implants in the Lumbar Spine," *World Spine II—Second Interdisciplinary Congress on Spine Care*, Aug., 2003, 2 pages.
Anatomy of the Lumbar Spine in MED TM MicroEndoscopic Discectomy (1997 Ludann Grand Rapids MI), 14 pgs.
Dirksmeier et al., "Microendoscopic and Open Laminotomy and Discectomy in Lumbar Disc Disease" *Seminars in Spine Surgery*, 1999, 11(2): 138-146.
METRx Delivered Order Form, 1999, 13 pages.
Medtronic Sofamor Danek "METRx™ MicroDisectomy System," *Medtronic Sofamor Danek USA*, 2000, 21 pgs.
Medtronic Sofamor Danek "METRx System Surgical Technique," 2004, 22 pages.
"MetRx System MicroEndoscopic Discectomy: An Evolution in Minimally Invasive Spine Surgery," *Sofamor Danek*, 1999, 6 pages.
Smith and Foley "MetRx System MicroEndoscopic Discectomy: Surgical Technique" *Medtronic Sofamor Danek*, 2000, 24 pages.
"Sofamor Danek MED Microendoscopic Discectomy System Brochure" including Rapp "New endoscopic lumbar technique improves access preserves tissue" Reprinted with permission from: *Orthopedics Today*, 1998, 18(1): 2 pages.
Japanese Patent Office JP Patent Application No. 2006-528306 Office Action with English Translation, Jun. 10, 2009, 4 pages.
Plaintiffs' Preliminary Invalidity Contentions re US Patents 7207949; 7470236 and 7582058, Sep. 18, 2009, 19 pages.
Plaintiffs' Preliminary Invalidity Contentions-Appendices, Sep. 18, 2009, 191 pages.
Plaintiffs' Supplemental Preliminary Invalidity Contentions re US Patents 7207949, 7470236, and 7582058, Sep. 29, 2009, 21 pages.
Plaintiffs' Supplemental Preliminary Invalidity Contentions-Appendices, Sep. 29, 2009, 294 pages.
Axon 501(k) Notification: Epoch 2000 Neurological Workstation, Dec. 3, 1997, 464 pages.
Foley and Smith, "Microendoscopic Discectomy," *Techniques in Neurosurgery*, 1997, 3(4):301-307.
Medtronic Sofamor Danek "UNION™ / UNION-L™ Anterior & Lateral Impacted Fusion Devices: Clear choice of stabilization," *Medtronic Sofamor Danek*, 2000, 4 pages.
NuVasive Vector™ Cannulae, 1 page (prior to Sep. 25, 2003).
NuVasive Triad™ 4 Tri-Columnar Spinal EndoArthrodesis™ via Minimally Invasive Guidance, 1 page (prior to Sep. 25 2003).
NuVasive Triad™ Cortical Bone Allograft, 1 page(prior to Sep. 25, 2003).
NuVasive Vertebral Body Access System, 1 page (prior to Sep. 25, 2003).
Marina, "New Technology for Guided Navigation with Real Time Nerve Surveillance for Minimally Invasive Spine Discectomy & Arthrodesis," *Spineline*, 2000, p. 39.
NuVasive "INS-1 Screw Test," 2001, 10 pages.
NuVasive letter re 510k Neuro Vision JJB System, Oct. 16, 2001, 5 pages.
NuVasive letter re 510k Guided Arthroscopy System, Oct. 5, 1999, 6 pages.
NuVasive letter re 510k INS-1 Intraoperative Nerve Surveillance System, Nov. 13, 2000, 7 pages.
"NuVasiveTM Receives Clearance to Market Two Key Elem Minimally Invasive Spine Surgery System," Nov. 27, 2001, 20 pages.
Schick et al., "Microendoscopic lumbar discectomy versus open surgery: an intraoperative EMG study," *Eur Spine J*, 2002, 11: 20-26.
NuVasive letter re: 510(k) for Neurovision JJB System (Summary), Sep. 25, 2001, 28 pages.
NuVasive letter re: Special 510(k) Premarket Notification: Neurovision JJB System (Device Description), Jul. 3, 2003, 18 pages.
NuVasive letter re: Special 510(k) Premarket Notification: Neurovision JJB System (Device Description), Mar. 1, 2004, 16 pages.
NuVasive letter re: Special 510(k) Premarket Notification: Neurovision JJB System (Device Description), May 26, 2005, 17 pages.
NuVasive letter re: 510(k) Premarket Notification: Neurovision JJB System (Device Description), Jun. 24, 2005, 16 pages.
NuVasive letter re: Special 510(k) Premarket Notification: Neurovision JJB System (Device Description), Sep. 14, 2006, 17 pages.
NuVasive 510(k) Premarket Notification: Neurovision JJB System (Device Description), Aug. 20, 2007, 8 pages.
NuVasive letter re: 510(k) Premarket Notification: Guided Spinal Arthroscopy System (Device Description), Feb. 1, 1999, 40 pages.
NuVasive 510(k) Premarket Notification: Spinal System (Summary), Apr. 12, 2004, 10 pages.
NuVasive 510(k) Summary NIM Monitor, Sep. 4, 1998, 4 pages.
NuVasive correspondence re 510(k) Premarket Notification INS-1 Intraoperative Nerve Surveillance System: Section IV Device Description, pp. 12-51 (prior to Sep. 25 2003).
NuVasive letter re 510(k) Premarket Notification INS-1 Intraoperative Nerve Surveillance System, Aug. 24, 2000, 81 pages.
Isley et al., "Recent Advances in Intraoperative Neuromonitoring of Spinal Cord Function: Pedicle Screw Stimulation Techniques," *American Journal of Electroneurodagnostic Technology*, Jun. 1997, 37(2):3-126.
Mathews et al., "Laparoscopic Discectomy with Anterior Lumbar Interbody Fusion," *Spine*, 1995, 20(16): 1797-1802.
Rose et al., "Persistently Electrified Pedicle Stimulation Instruments in Spinal Instrumentation: Techniques and Protocol Development," *Spine*, 1997, 22(3): 334-343.
"Electromyography System," International Search report from International Application No. PCT/US00/32329, Apr. 27, 2001, 9 pages.
"Nerve Proximity and Status Detection System and Method," International Search Report from International Application No. PCT/US01/18606, Oct. 18, 2001, 6 pages.
"Relative Nerve Movement and Status Detection System and Method," International Search Report from International Application No. PCT/US01/18579, Jan. 15, 2002, 6 pages.
"System and Method for Determining Nerve Proximity Direction and Pathology During Surgery," International Search Report from International Application No. PCT/US02/22247, Mar. 27, 2003, 4 pages.
"System and Methods for Determining Nerve Direction to a Surgical Instrument," International Search Report from International Application No. PCT/US03/02056, Aug. 12, 2003, 5 pages.
"Systems and Methods for Performing Percutaneous Pedicle Integrity Assessments," International Search Report from International Application No. PCT/US02/35047, Aug. 11, 2003, 5 pages.
"Systems and Methods for Performing Surgery Procedures and Assessments," International Search Report from International Application No. PCT/US02/30617, Jun. 5, 2003, 4 pages.
Lenke et al., "Triggered Electromyographic Threshold for Accuracy of Pedicle Screw Placement," *Spine*, 1995, 20(4): 1585-1591.
"Brackmann II EMG System," *Medical Electronics*, 1999, 4 pages.
"Neurovision SE Nerve Locator/Monitor", RLN Systems Inc. Operators Manual, 1999, 22 pages.
"The Brackmann II EMG Monitoring System," Medical Electronics Co. Operator's Manual Version 1.1, 1995, 50 pages.
"The Nicolet Viking IV," Nicolet Biomedical Products, 1999, 6 pages.
Anderson et al., "Pedicle screws with high electrical resistance: a potential source of error with stimulus-evoked EMG," *Spine*, Department of Orthopaedic Surgery University of Virginia, Jul. 15, 2002, 27(14): 1577-1581.
Bose et al., "Neurophysiologic Monitoring of Spinal Nerve Root Function During Instrumented Posterior Lumber Spine Surgery," *Spine*, 2002, 27(13):1444-1450.
Calancie et al., "Stimulus-Evoked EMG Monitoring During Transpedicular Lumbosacral Spine Instrumentation" *Spine*, 1994, 19(24): 2780-2786.
Clements et al., "Evoked and Spontaneous Electromyography to Evaluate Lumbosacral Pedicle Screw Placement," *Spine*, 1996, 21(5): 600-604.
Danesh-Clough et al. ,"The Use of Evoked EMG in Detecting Misplaced Thoracolumbar Pedicle Screws," *Spine*, Orthopaedic Department Dunedin Hospital, Jun. 15, 2001, 26(12): 1313-1316.

Darden et al., "A Comparison of Impedance and Electromyogram Measurements in Detecting the Presence of Pedicle Wall Breakthrough", *Spine*, Charlotte Spine Center North Carolina, Jan. 15, 1998, 23(2): 256-262.

Ebraheim et al., "Anatomic Relations Between the Lumbar Pedicle and the Adjacent Neural Structures," *Spine*, Department of Orthopaedic Surgery Medical College of Ohio, Oct. 15, 1997, 22(20): 2338-2341.

Ford et al. "Electrical Characteristics of Peripheral Nerve Stimulators Implications for Nerve Localization," *Regional Anesthesia*, 1984, 9: 73-77.

Glassman et al., "A Prospective Analysis of Intraoperative Electromyographic Monitoring of Pepticle Screw Placement With Computed Tomographic Scan Confirmation," *Spine*, 1995, 20(12): 1375-1379.

Greenblatt et al., "Needle Nerve Stimulator-Locator: Nerve Blocks with a New Instrument for Locating Nerves," *Anesthesia& Analgesia*, 1962, 41(5): 599-602.

Haig, "Point of view," *Spine*, 2002, 27(24): 2819.

Haig et al., "The Relation Among Spinal Geometry on MRI, Paraspinal Electromyographic for Abnormalities, and Age in Persons Referred for Electrodiagnostic Testing of Low Back Symptoms," *Spine*, Department of Physical Medicine and Rehabilitation University of Michigan, Sep. 1, 2002, 27(17): 1918-1925.

Holland et al., "Higher Electrical Stimulus Intensities are Required to Activate Chronically Compressed Nerve Roots: Implications for Intraoperative Electromyographic Pedicle Screw Testing," *Spine*, Department of Neurology, Johns Hopkins University School of Medicine, Jan. 15, 1998, 23(2): 224-227.

Holland, "Intraoperative Electromyography During Thoracolumbar Spinal Surgery," *Spine*, 1998, 23(17): 1915-1922.

Maguire et al., "Evaluation of Intrapedicular Screw Position Using Intraoperative Evoked Electromyography," *Spine*, 1995, 20(9): 1068-1074.

Martin et al. "Initiation of Erection and Semen Release by Rectal Probe Electrostimulation (RPE)," *The Journal of Urology*, The Williams& Wilkins Co., 1983, 129: 637-642.

Minahan et al., "The Effect of Neuromuscular Blockade on Pedicle Screw Stimulation Thresholds" *Spine*, Department of Neurology, Johns Hopkins University School of Medicine, Oct. 1, 2000, 25(19): 2526-2530.

Pither et al., "The Use of Peripheral Nerve Stimulators for Regional Anesthesia: Review of Experimental Characteristics Technique and Clinical Applications," *Regional Anesthesia*, 1985, 10:49-58.

Raj et al., "Infraclavicular Brachial Plexus Block—A New Approach" *Anesthesia and Analgesia*, 1973, (52)6: 897-904.

Raj et al., "The Use of Peripheral Nerve Stimulators for Regional Anesthesia," *Clinical Issues in Regional Anesthesia*, 1985, 1(4):1-6.

Raj et al., "Use of the Nerve Stimulator for Peripheral Blocks," *Regional Anesthesia*, Apr.-Jun. 1980, pp. 14-21.

Raymond et al., "The Nerve Seeker: A System for Automated Nerve Localization," *Regional Anesthesia*, 1992, 17(3): 151-162.

Shafik, "Cavernous Nerve Simulation through an Extrapelvic Subpubic Approach: Role in Penile Erection," *Eur. Urol*, 1994, 26: 98-102.

Toleikis et al., "The Usefulness of Electrical Stimulation for Assessing Pedicle Screw Replacements," *Journal of Spinal Disorder*, 2000, 13(4): 283-289.

Journee et al., "System for Intra-Operative Monitoring of the Cortical Integrity of the Pedicle During Pedicle Screw Placement in Low-Back Surgery: Design and Clinical Results," *Sensory and Neuromuscular Diagnostic Instrumentation and Data Analysis I, 18th Annual International Conference on Engineering in Medicine and Biology Society*, Amsterdam, 1996, pp. 144-145.

Medtronic Sofamor Danek "UNION™ / UNION-L™ Anterior & Lateral Impacted Fusion Devices: Surgical Technique" *Medtronic Sofamor Danek*, 2001, 20 pages.

Defendant's Disclosure of Asserted Claims and Preliminary Infringement Contentions Regarding USP 7207949; 7470236 and 7582058, Aug. 31, 2009, 21 pages.

Brau, "Chapter 22: Anterior Retroperitoneal Muscle-Sparing approach to L2-S1 of the Lumbar Spine," *Surgical Approaches to the Spine*. Robert G. Watkins, MD. (ed) 2003, pp. 165-181.

Kossmann et al., "Minimally Invasive Vertebral Replacement with Cages in Thoracic and Lumbar Spine," *European Journal of Trauma*, 2001, 27: 292-300.

Mayer H. M. (ed.) *Minimally Invasive Spine Surgery: A Surgical Manual*. 2000. 51 pages.

Pimenta et al., "Implante de protese de nucleo pulpost: analise inicial," *Journal Brasileiro de Neurocirurgia*, 2001, 12(2): 93-96..

Traynelis, "Spinal Arthroplasty," *Neurological Focus*, 2002, 13(2): 12 pages.

Zdeblick, Thomas A. (ed.). Anterior Approaches to the Spine. 1999. 43 pages.

Amended Complaint for *NuVasive, Inc. v. Globus Medical, Inc.*, Case No. 1:10-cv-0849 (D. Del., Oct. 5, 2010), 28 pages.

Request for *Inter Partes* Reexamination in re: U.S. Patent 7,691,057, dated Feb. 8, 2012, 50 pages.

* cited by examiner

SURGICAL ACCESS SYSTEM AND RELATED METHODS

CROSS-REFERENCES TO RELATED APPLICATIONS

This application is a continuation of U.S. patent application Ser. No. 10/759,811 (now U.S. Pat. No. 7,691,057), filed on Jan. 16, 2004, which is claims priority to U.S. Provisional patent application Ser. No. 60/440,905, filed Jan. 16, 2003, the entire contents of which are hereby expressly incorporated by reference into this disclosure as if set forth fully herein. The present application also incorporates by reference the following commonly owned patent applications in their entireties (collectively, the "NeuroVision Applications"): PCT App. Ser. No. PCT/US02/22247, entitled "System and Methods for Determining Nerve Proximity, Direction, and Pathology During Surgery," filed on Jul. 11, 2002; PCT App. Ser. No. PCT/US02/30617, entitled "System and Methods for Performing Surgical Procedures and Assessments," filed on Sep. 25, 2002; PCT App. Ser. No. PCT/US02/35047, entitled "System and Methods for Performing Percutaneous Pedicle Integrity Assessments," filed on Oct. 30, 2002; PCT App. Ser. No. PCT/US03/02056, entitled "System and Methods for Determining Nerve Direction to a Surgical Instrument," filed Jan. 15, 2003 (collectively "NeuroVision PCT Applications").

BACKGROUND OF THE INVENTION

I. Field of the Invention

The present invention relates generally to systems and methods for performing surgical procedures and, more particularly, for accessing a surgical target site in order to perform surgical procedures.

II. Discussion of the Prior Art

A noteworthy trend in the medical community is the move away from performing surgery via traditional "open" techniques in favor of minimally invasive or minimal access techniques. Open surgical techniques are generally undesirable in that they typically require large incisions and high amounts of tissue displacement to gain access to the surgical target site, which produces concomitantly high amounts of pain, lengthened hospitalization (increasing health care costs), and high morbidity in the patient population. Less-invasive surgical techniques (including so-called "minimal access" and "minimally invasive" techniques) are gaining favor due to the fact that they involve accessing the surgical target site via incisions of substantially smaller size with greatly reduced tissue displacement requirements. This, in turn, reduces the pain, morbidity and cost associated with such procedures. The access systems developed to date, however, fail in various respects to meet all the needs of the surgeon population.

One drawback associated with prior art surgical access systems relates to the ease with which the operative corridor can be created, as well as maintained over time, depending upon the particular surgical target site. For example, when accessing surgical target sites located beneath or behind musculature or other relatively strong tissue (such as, by way of example only, the psoas muscle adjacent to the spine), it has been found that advancing an operative corridor-establishing instrument directly through such tissues can be challenging and/or lead to unwanted or undesirable effects (such as stressing or tearing the tissues). While certain efforts have been undertaken to reduce the trauma to tissue while creating an operative corridor, such as (by way of example only) the sequential dilation system of U.S. Pat. No. 5,792,044 to Foley et al., these attempts are nonetheless limited in their applicability based on the relatively narrow operative corridor. More specifically, based on the generally cylindrical nature of the so-called "working cannula," the degree to which instruments can be manipulated and/or angled within the cannula can be generally limited or restrictive, particularly if the surgical target site is a relatively deep within the patient.

Efforts have been undertaken to overcome this drawback, such as shown in U.S. Pat. No. 6,524,320 to DiPoto, wherein an expandable portion is provided at the distal end of a cannula for creating a region of increased cross-sectional area adjacent to the surgical target site. While this system may provide for improved instrument manipulation relative to sequential dilation access systems (at least at deep sites within the patient), it is nonetheless flawed in that the deployment of the expandable portion may inadvertently compress or impinge upon sensitive tissues adjacent to the surgical target site. For example, in anatomical regions having neural and/or vasculature structures, such a blind expansion may cause the expandable portion to impinge upon these sensitive tissues and cause neural and/or vasculature compromise, damage and/or pain for the patient.

This highlights yet another drawback with the prior art surgical access systems, namely, the challenges in establishing an operative corridor through or near tissue having major neural structures which, if contacted or impinged, may result in neural impairment for the patient. Due to the threat of contacting such neural structures, efforts thus far have largely restricted to establishing operative corridors through tissue having little or substantially reduced neural structures, which effectively limits the number of ways a given surgical target site can be accessed. This can be seen, by way of example only, in the spinal arts, where the exiting nerve roots and neural plexus structures in the psoas muscle have rendered a lateral or far lateral access path (so-called trans-psoas approach) to the lumbar spine virtually impossible. Instead, spine surgeons are largely restricted to accessing the spine from the posterior (to perform, among other procedures, posterior lumbar interbody fusion (PLIF)) or from the anterior (to perform, among other procedures, anterior lumbar interbody fusion (ALIF)).

Posterior-access procedures involve traversing a shorter distance within the patient to establish the operative corridor, albeit at the price of oftentimes having to reduce or cut away part of the posterior bony structures (i.e. lamina, facets, spinous process) in order to reach the target site (which typically comprises the disc space). Anterior-access procedures are relatively simple for surgeons in that they do not involve reducing or cutting away bony structures to reach the surgical target site. However, they are nonetheless disadvantageous in that they require traversing through a much greater distance within the patient to establish the operative corridor, oftentimes requiring an additional surgeon to assist with moving the various internal organs out of the way to create the operative corridor.

The present invention is directed at eliminating, or at least minimizing the effects of, the above-identified drawbacks in the prior art.

SUMMARY OF THE INVENTION

The present invention accomplishes this goal by providing a novel access system and related methods which, according to one embodiment, involves detecting the existence of (and optionally the distance and/or direction to) neural structures before, during, and after the establishment of an operative corridor through (or near) any of a variety of tissues having such neural structures which, if contacted or impinged, may otherwise result in neural impairment for the patient. It is expressly noted that, although described herein largely in terms of use in spinal surgery, the access system of the present invention is suitable for use in any number of additional surgical procedures wherein tissue having significant neural structures must be passed through (or near) in order to establish an operative corridor.

The present invention accomplishes this goal by providing a novel access system and related methods which involve: (1) distracting the tissue between the patient's skin and the surgical target site to create an area of distraction (otherwise referred to herein as a "distraction corridor"); (2) retracting the distraction corridor to establish and maintain an operative corridor; and/or (3) detecting the existence of (and optionally the distance and/or direction to) neural structures before, during and after the establishment of the operative corridor through (or near) any of a variety of tissues having such neural structures which, if contacted or impinged, may otherwise result in neural impairment for the patient.

As used herein, "distraction" or "distracting" is defined as the act of creating a corridor (extending to a location at or near the surgical target site) having a certain cross-sectional area and shape ("distraction corridor"), and "retraction" or "retracting" is defined as the act of creating an operative corridor by increasing or maintaining the cross-sectional area of the distraction corridor (and/or modifying its shape) with at least one retractor blade such that surgical instruments can be passed through operative corridor to the surgical target site.

According to one broad aspect of the present invention, the access system comprises a tissue distraction assembly and a tissue retraction assembly, both of which may be equipped with one or more electrodes for use in detecting the existence of (and optionally the distance and/or direction to) neural structures during the steps tissue distraction and/or retraction. To accomplish this, one or more stimulation electrodes are provided on the various components of the distraction assemblies and/or retraction assemblies, a stimulation source (e.g. voltage or current) is coupled to the stimulation electrodes, a stimulation signal is emitted from the stimulation electrodes as the various components are advanced towards the surgical target site, and the patient is monitored to determine if the stimulation signal causes muscles associated with nerves or neural structures within the tissue to innervate. If the nerves innervate, this indicates that neural structures may be in close proximity to the distraction and/or retraction assemblies.

This monitoring may be accomplished via any number of suitable fashions, including but not limited to observing visual twitches in muscle groups associated with the neural structures likely to found in the tissue, as well as any number of monitoring systems. In either situation (traditional EMG or surgeon-driven EMG monitoring), the access system of the present invention may advantageously be used to traverse tissue that would ordinarily be deemed unsafe or undesirable, thereby broadening the number of manners in which a given surgical target site may be accessed.

The tissue distraction assembly is capable of, as an initial step, distracting a region of tissue between the skin of the patient and the surgical target site. The tissue retraction assembly is capable of, as a secondary step, being introduced into this distracted region to thereby define and establish the operative corridor. Once established, any of a variety of surgical instruments, devices, or implants may be passed through and/or manipulated within the operative corridor depending upon the given surgical procedure. The electrode(s) are capable of, during both tissue distraction and retraction, detecting the existence of (and optionally the distance and/or direction to) neural structures such that the operative corridor may be established through (or near) any of a variety of tissues having such neural structures which, if contacted or impinged, may otherwise result in neural impairment for the patient. In this fashion, the access system of the present invention may be used to traverse tissue that would ordinarily be deemed unsafe or undesirable, thereby broadening the number of manners in which a given surgical target site may be accessed.

The tissue distraction assembly may include any number of components capable of performing the necessary distraction. By way of example only, the tissue distraction assembly may include a K-wire, an initial dilator (of split construction or traditional non-slit construction), and one or more dilators of traditional (that is, non-split) construction for performing the necessary tissue distraction to receive the remainder of the tissue retractor assembly thereafter. One or more electrodes may be provided on one or more of the K-wire and dilator(s) to detect the presence of (and optionally the distance and/or direction to) neural structures during tissue distraction.

The tissue retraction assembly may include any number of components capable of performing the necessary retraction. By way of example only, the tissue retraction assembly may include one or more retractor blades extending proximally from the surgical target site for connection with a pivot linkage assembly. The pivot linkage includes first and second pivot arms capable of maintaining the retractor blades in a first, closed position to facilitate the introduction of the retractor blades over the distraction assembly. Thereafter, the pivot linkage may be manipulated to open the retractor assembly; that is, allowing the retractor blades to separate from one another (preferably simultaneously) to create an operative corridor to the surgical target site. In a preferred embodiment, this is accomplished by maintaining a posterior retractor blade in a fixed position relative to the surgical target site (so as to avoid having it impinge upon any exiting nerve roots near the posterior elements of the spine) while the additional retractor blades (i.e. cephalad, caudal and/or anterior retractor blades) are moved or otherwise translated away from the posterior retractor blade (and each other) so as to create the operative corridor in a fashion that doesn't infringe upon the region of the exiting nerve roots. This is accomplished, in part, through the use of a secondary pivot linkage coupled to the pivot linkage assembly, which allows the posterior retractor blade to remain in a constant position while the other retractor blades are moved. In one embodiment, the anterior retractor blade may be positioned after the posterior, cephalad, and caudal retractor blades are positioned into the fully retracted position. This may be accomplished by coupling the anterior refractor blade to the pivot linkage via an arm assembly.

The retractor blades may be optionally dimensioned to receive and direct a rigid shim element to augment the structural stability of the retractor blades and thereby ensure the operative corridor, once established, will not decrease or become more restricted, such as may result if distal ends of the retractor blades were permitted to "slide" or otherwise move in response to the force exerted by the displaced tissue. In a preferred embodiment, only the posterior and anterior retractor blades are equipped with such rigid shim elements, which are advanced into the disc space after the posterior and anterior retractor blades are positioned (posterior first, followed by anterior after the cephalad, caudal and anterior blades are moved into the fully retracted position). The rigid shim elements are preferably oriented within the disc space such that they distract the adjacent vertebral bodies, which serves to restore disc height. They are also preferably advanced a sufficient distance within the disc space (preferably past the midline), which serves the dual purpose of preventing post-operative scoliosis and forming a protective barrier (preventing the migration of tissue (such as nerve roots) into the operative field and the inadvertent advancement of instruments outside the operative field).

The retractor blades may optionally be equipped with a mechanism for transporting or emitting light at or near the surgical target site to aid the surgeon's ability to visualize the surgical target site, instruments and/or implants during the given surgical procedure. According to one embodiment, this mechanism may comprise, but need not be limited to, providing one or more strands of fiber optic cable within the walls of the retractor blades such that the terminal (distal) ends are capable of emitting light at or near the surgical target site. According to another embodiment, this mechanism may comprise, but need not be limited to, constructing the retractor blades of suitable material (such as clear polycarbonate) and configuration such that light may be transmitted generally distally through the walls of the retractor blade light to shine light at or near the surgical target site. This may be performed by providing the retractor blades having light-transmission characteristics (such as with clear polycarbonate construction) and transmitting the light almost entirely within the walls of the retractor blade (such as by frosting or otherwise rendering opaque portions of the exterior and/or interior) until it exits a portion along the interior (or medially-facing) surface of the retractor blade to shine at or near the surgical target site. The exit portion may be optimally configured such that the light is directed towards the approximate center of the surgical target site and may be provided along the entire inner periphery of the retractor blade or one or more portions therealong.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Figure 1:
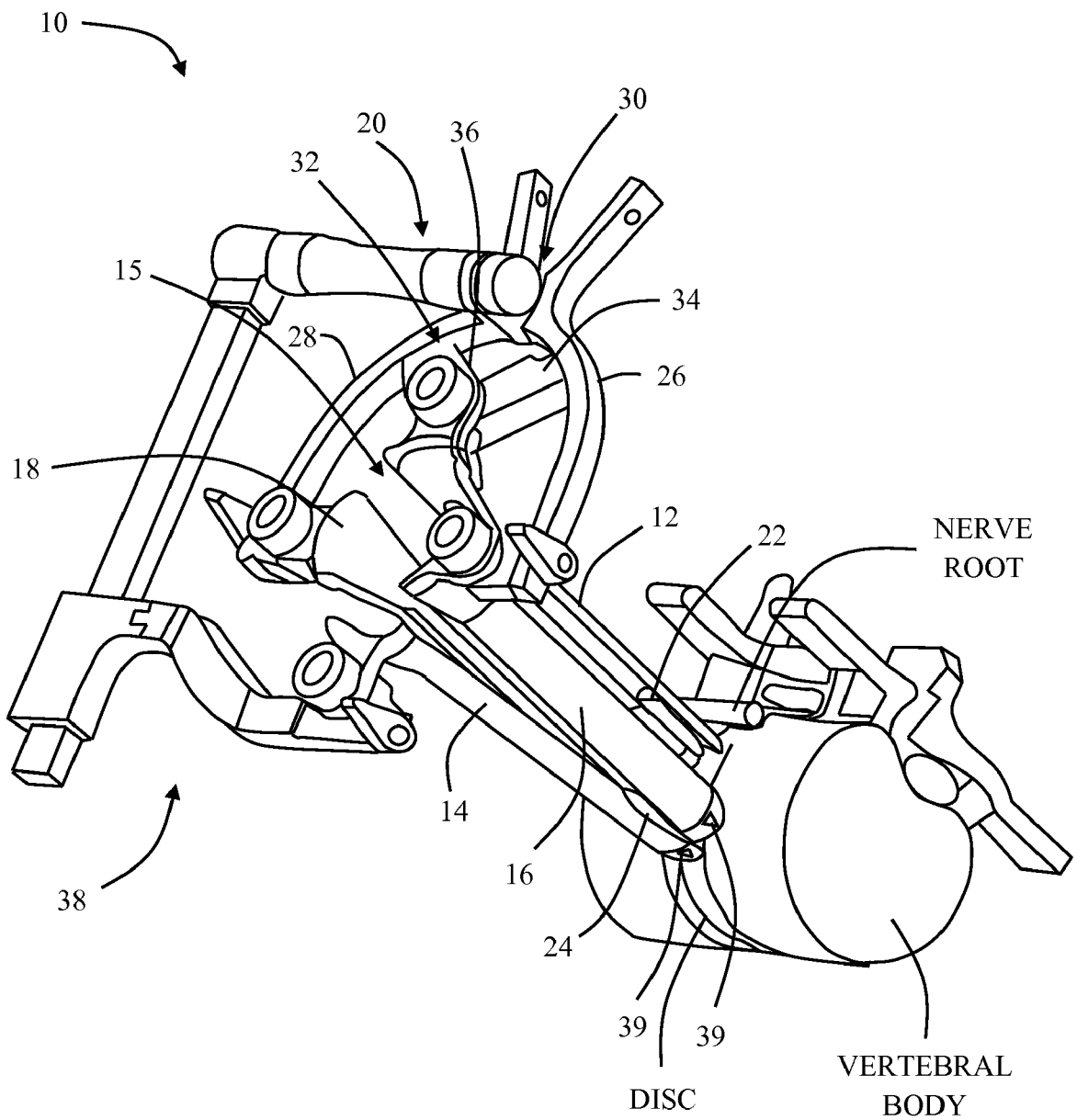
FIG. 1 is a perspective view of a tissue retraction assembly (in use) forming part of a surgical access system according to the present invention.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. It is furthermore to be readily understood that, although discussed below primarily within the context of spinal surgery, the surgical access system of the present invention may be employed in any number of anatomical settings to provide access to any number of different surgical target sites throughout the body. The surgical access system disclosed herein boasts a variety of inventive features and components that warrant patent protection, both individually and in combination.

It is furthermore to be readily understood that, although discussed below primarily within the context of spinal surgery, the surgical access system and related methods of the present invention may find applicability in any of a variety of surgical and/or medical applications such that the following description relative to the spine is not to be limiting of the overall scope of the present invention. Moreover, while described below employing the nerve monitoring features described above (otherwise referred to as "nerve surveillance") during spinal surgery, it will be appreciated that such nerve surveillance will not be required in all situations, depending upon the particular surgical target site (e.g. disk space, vertebral body, and/or internal organ), surgical approach (e.g. lateral, posterior, anterior, and/or postero-lateral approaches to the spine), and spinal level (e.g. cervical, thoracic and/or lumbar).

The present invention is directed at a novel surgical access system and related methods which involve creating and maintaining an operative corridor to the surgical target site, and optionally detecting the existence of (and optionally the distance and/or direction to) neural structures before, during and/or after this process (including the steps of distraction and/or retraction). This is accomplished by employing the following steps: (1) one or more stimulation electrodes are provided on the various distraction and/or retraction components; (2) a stimulation source (e.g. voltage or current) is coupled to the stimulation electrodes; (3) a stimulation signal is emitted from the stimulation electrodes as the various components are advanced towards or maintained at or near the surgical target site; and (4) the patient is monitored to determine if the stimulation signal causes muscles associated with nerves or neural structures within the tissue to innervate. If the nerves innervate, this may indicate that neural structures may be in close proximity to the distraction and/or retraction components.

Neural monitoring may be accomplished via any number of suitable fashions, including but not limited to observing visual twitches in muscle groups associated with the neural structures likely to found in the tissue, as well as any number of monitoring systems, including but not limited to any commercially available "traditional" electromyography (EMG) system (that is, typically operated by a neurophysiologist. Such monitoring may also be carried out via the surgeon-driven EMG monitoring system shown and described in the following commonly owned and co-pending "NeuroVision Applications" incorporated by reference into this disclosure above. In any case (visual monitoring, traditional EMG and/or surgeon-driven EMG monitoring), the access system of the present invention may advantageously be used to traverse tissue that would ordinarily be deemed unsafe or undesirable, thereby broadening the number of manners in which a given surgical target site may be accessed.

Distraction followed by retraction is advantageous because it provides the ability to more easily position an operative corridor-establishing device through tissue that is strong, thick or otherwise challenging to traverse in order to access a surgical target site. The various distraction systems of the present invention are advantageous in that they provide an improved manner of atraumatically establishing a distraction corridor prior to the use of the retraction systems of the present invention. The various retractor systems of the present invention are advantageous in that they provide an operative corridor having improved cross-sectional area and shape (including customization thereof) relative to the prior art surgical access systems. Moreover, by optionally equipping the various distraction systems and/or retraction systems with one or more electrodes, an operative corridor may be established through (or near) any of a variety of tissues having such neural structures which, if contacted or impinged, may otherwise result in neural impairment for the patient.

The present invention involves accessing a surgical target site in a fashion less invasive than traditional "open" surgeries and doing so in a manner that provides access in spite of the neural structures required to be passed through (or near) in order to establish an operative corridor to the surgical target site. Generally speaking, the surgical access system of the present invention accomplishes this by providing a tissue distraction assembly and a tissue retraction assembly, both of which may be equipped with one or more electrodes for use in detecting the existence of (and optionally the distance and/or direction to) neural structures.

These electrodes are preferably provided for use with a nerve surveillance system such as, by way of example, the type shown and described in co-pending and commonly assigned NeuroVision PCT Applications incorporated by reference above. Generally speaking, this nerve surveillance system is capable of detecting the existence of (and optionally the distance and/or direction to) neural structures during the distraction and retraction of tissue by detecting the presence of nerves by applying a stimulation signal to such instruments and monitoring the evoked EMG signals from the myotomes associated with the nerves being passed by the distraction and retraction systems of the present invention. In so doing, the system as a whole (including the surgical access system of the present invention) may be used to form an operative corridor through (or near) any of a variety of tissues having such neural structures, particularly those which, if contacted or impinged, may otherwise result in neural impairment for the patient. In this fashion, the access system of the present invention may be used to traverse tissue that would ordinarily be deemed unsafe or undesirable, thereby broadening the number of manners in which a given surgical target site may be accessed.

The tissue distraction assembly of the present invention (comprising a K-wire, an initial dilator, and a split-dilator disposed within the initial dilator) is employed to distract the tissues extending between the skin of the patient and a given surgical target site (preferably along the posterior region of the target intervertebral disc). A secondary distraction assembly (i.e. a plurality of sequentially dilating cannulae) may optionally be employed after the initial distraction assembly to further distract the tissue. Once distracted, the resulting void or distracted region within the patient is of sufficient size to accommodate a tissue retraction assembly of the present invention. More specifically, the tissue retraction assembly (comprising a plurality of retractor blades coupled to a linkage assembly) may be advanced relative to the secondary distraction assembly such that the retractor blades, in a first, closed position, are advanced over the exterior of the secondary distraction assembly. At that point, the linkage assembly may be operated to move the retractor blades into a second, open or "retracted" position to create an operative corridor to the surgical target site.

According to one aspect of the invention, following (or before) this retraction, a posterior shim element (which is preferably slideably engaged with the posterior retractor blade) may be advanced such that a shim extension in positioned within the posterior region of the disc space. If done before retraction, this helps ensure that the posterior retractor blade will not move posteriorly during the retraction process, even though the other retractor blades (i.e. cephalad, caudal, and/or anterior retractor blades) are able to move and thereby create an operative corridor. Fixing the posterior retractor blade in this fashion helps prevent inadvertent contact with the existing nerve roots in the posterior region of the spine. The posterior shim element also helps ensure that surgical instruments employed within the operative corridor are incapable of being advanced outside the operative corridor, yet again preventing inadvertent contact with the exiting nerve roots during the surgery. Once in the appropriate anterior position, the anterior retractor blade may be locked in position and, thereafter, an anterior shim element advanced therealong for positioning a shim extension within the anterior of the disc space.

The shim elements serve to distract the adjacent vertebral bodies (thereby restoring disc height), to form protective barriers (against the migration of tissue into (or instruments out of) the operative site), and to rigidly couple the posterior and anterior retractor blades in fixed relation relative to the vertebral bodies. Once the operative corridor is established, any of a variety of surgical instruments, devices, or implants may be passed through and/or manipulated within the operative corridor depending upon the given surgical procedure.

Figure 9:
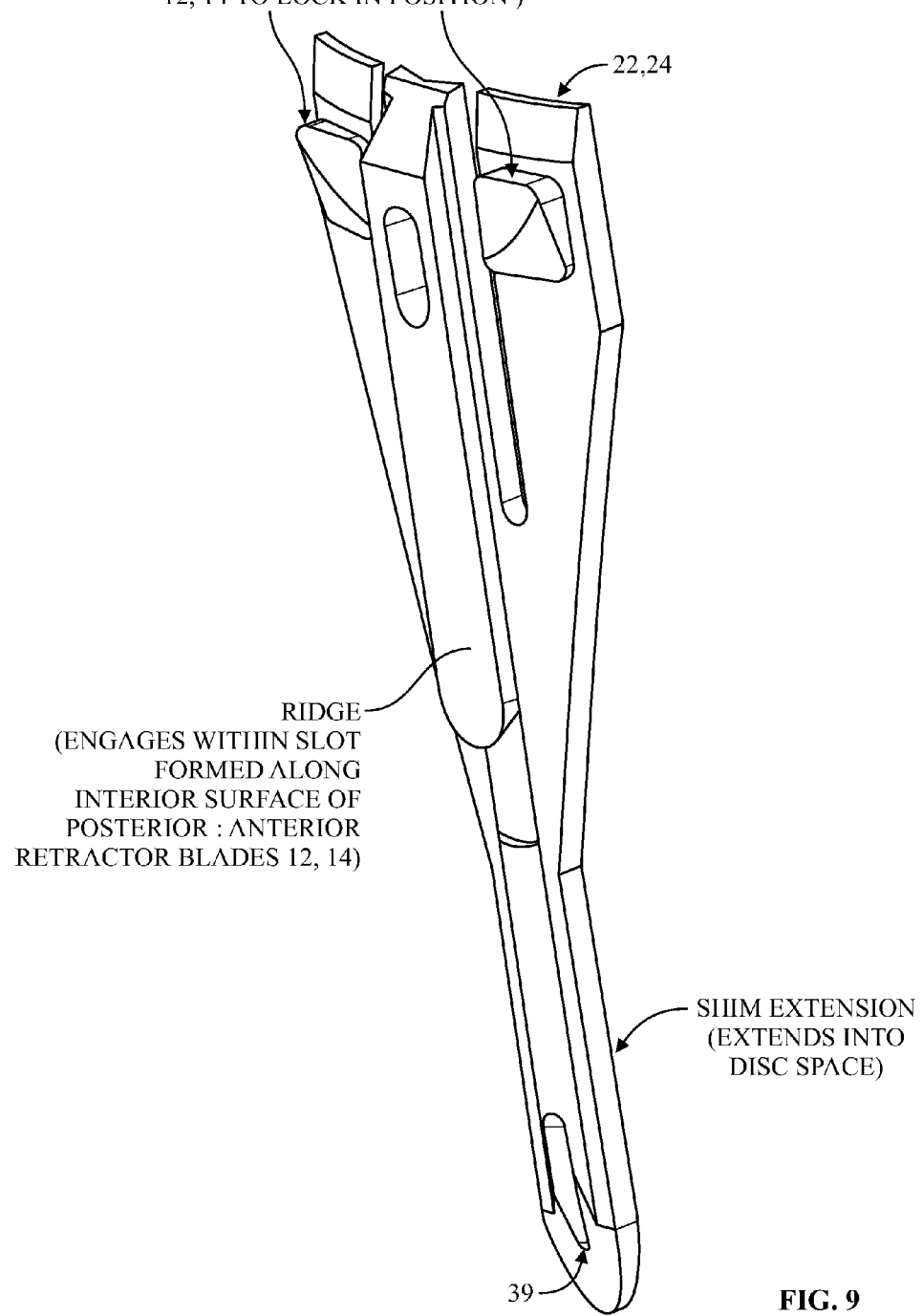
FIG. 9 is a back view of a shim element according to the present invention dimensioned to be engaged with the inner surface of the posterior (and optionally anterior) retractor blade for the purpose of positioning a shim extension within the disc space, such as via the shim introducer shown in FIG. 8.

FIG. 1 illustrates a tissue retraction assembly 10 forming part of a surgical access system according to the present invention. The retraction assembly 10 includes a posterior retractor blade 12, an anterior refractor blade 14, cephalad refractor blade 16, and caudal retractor blade 18, all of which are coupled to a linkage assembly 20. Posterior and anterior retractor blades 12, 14 establish an AP (or "width") dimension of an operative corridor 15. Posterior retractor blade 12 and anterior retractor blade 14 are equipped with shim elements 22, 24, respectively (shown more clearly in FIG. 9). Shim elements 22, 24 serve to distract the adjacent vertebral bodies (thereby restoring disc height), form protective barriers (against the migration of tissue into (or instruments out of) the operative site), and rigidly couple the posterior and anterior retractor blades 12, 14 in fixed relation relative to the vertebral bodies. Cephalad and caudal retractor blades 16, 18 establish and maintain the "height" dimension of the operative corridor 15. Each retractor blade 12-18 (and optionally the shim elements 22, 24) may be, according to the present invention, provided with one or more electrodes 39 (preferably at their distal regions) equipped for use with a nerve surveillance system, such as, by way of example, the type shown and described in the NeuroVision PCT Applications.

The linkage assembly 20 may be coupled to any number of mechanisms for rigidly registering the linkage assembly 20 in fixed relation to the operative site, such as through the use of an articulating arm mounted to the operating table. The linkage assembly 20 includes first and second arm members 26, 28 hingedly coupled at 30. The cephalad retractor blade 16 is rigidly coupled (generally perpendicularly) to the end of the first arm member 26. The caudal retractor blade 18 is rigidly coupled (generally perpendicularly) to the end of the second arm member 28. The posterior retractor blade 12 is coupled to the linkage assembly 20 via a pivot linkage 32 (comprising a first arm 34 hingedly disposed between the posterior refractor blade 12 and the first arm member 26, and a second arm 26 hingedly disposed between the posterior retractor blade 12 and the second arm 28) such that the posterior retractor blade 12 will have a tendency to remain in the same position during the retraction process. According to one embodiment, the anterior retractor blade 14 may be coupled to the linkage assembly 20 via an arm assembly 38.

Figure 2:
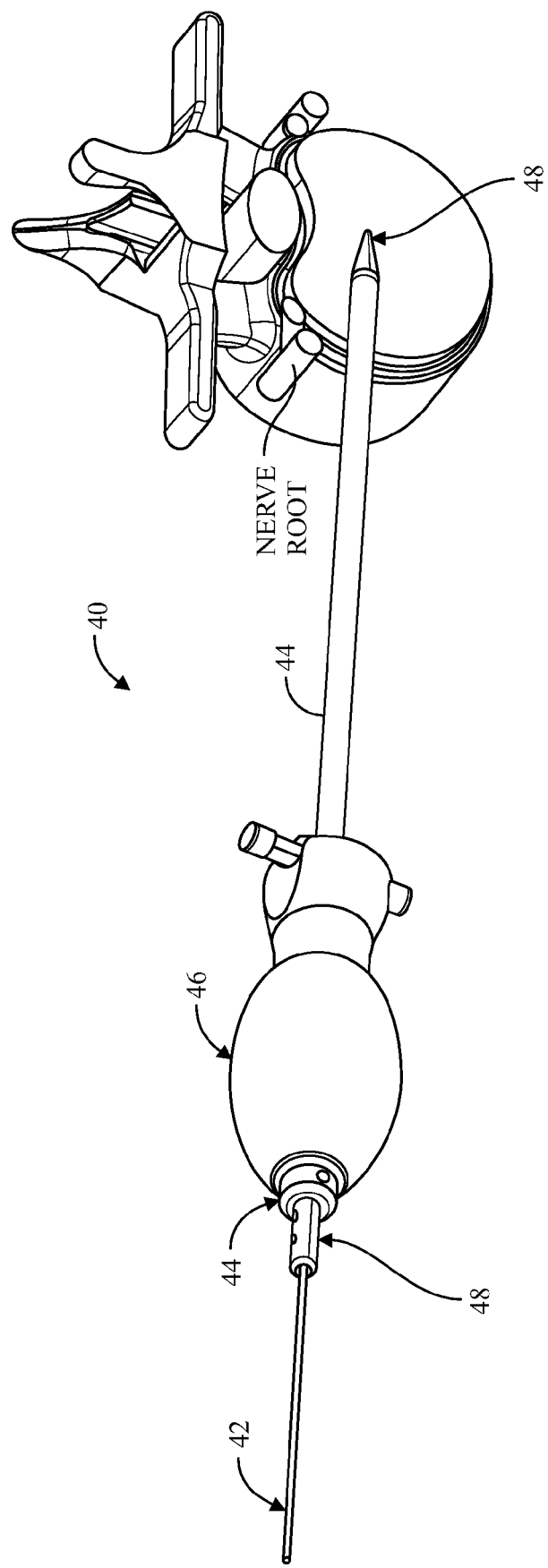
FIG. 2 is a perspective view illustrating the components and use of an initial distraction assembly (i.e. K-wire, an initial dilating cannula with handle, and a split-dilator housed within the initial dilating cannula) forming part of the surgical access system according to the present invention, for use in distracting to a surgical target site (i.e. annulus)
Figure 3:
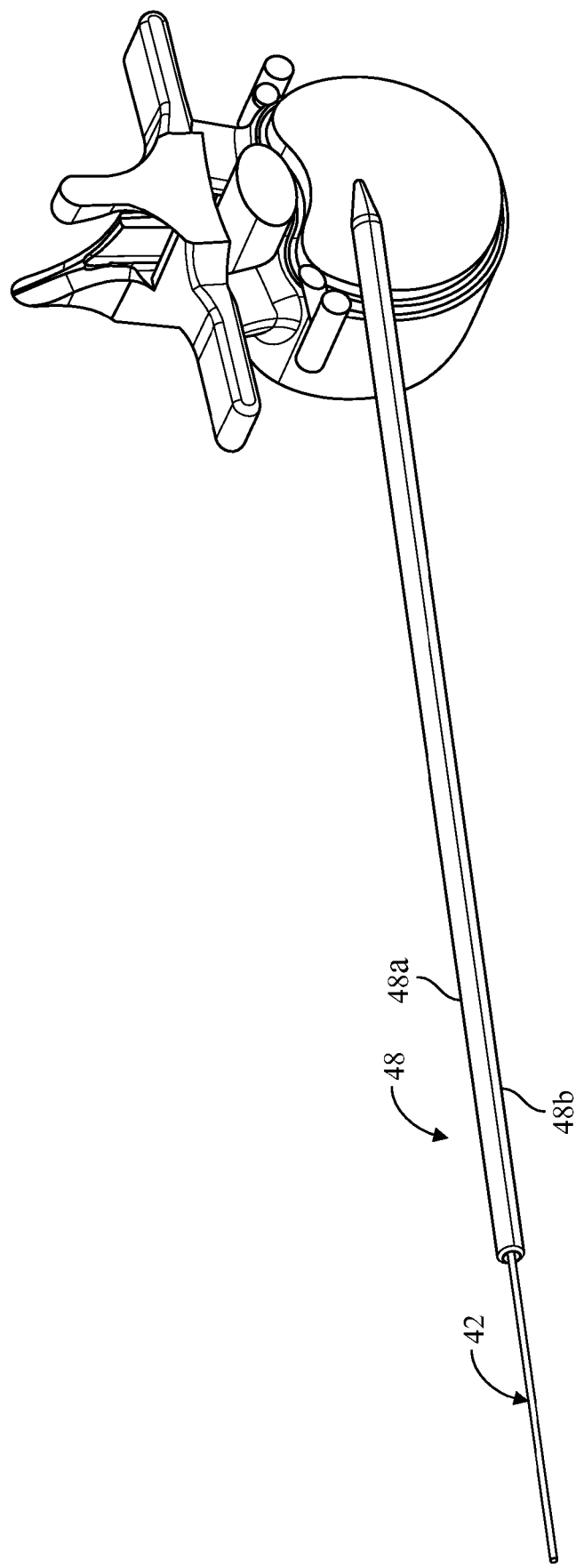
FIG. 3 is a perspective view illustrating the K-wire and split-dilator of the initial distraction assembly with the initial dilating cannula and handle removed.
Figure 4:
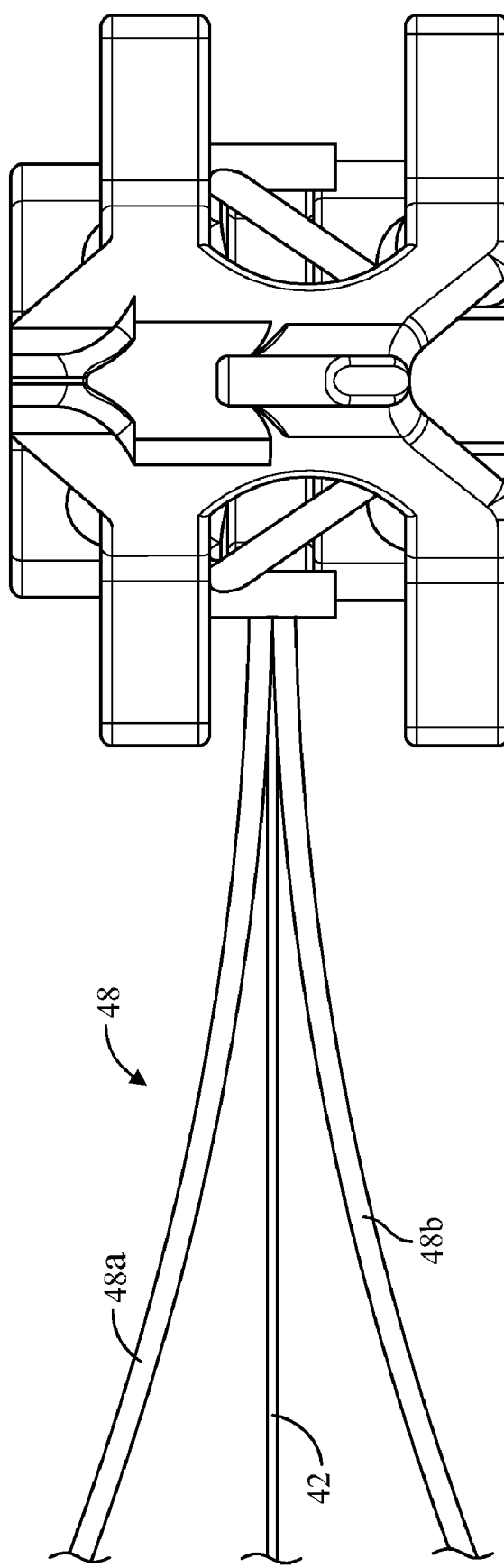
FIG. 4 is a posterior view of the vertebral target site illustrating the split-dilator of the present invention in use distracting in a generally cephalad-caudal fashion according to one aspect of the present invention.

FIG. 2 illustrates an initial distraction assembly 40 forming part of the surgical access system according to the present invention. The initial distraction assembly 40 includes a K-wire 42, an initial dilating cannula 44 with handle 46, and a split-dilator 48 housed within the initial dilating cannula 44. In use, the K-wire 42 and split-dilator 48 are disposed within the initial dilating cannula 44 and the entire assembly 40 advanced through the tissue towards the surgical target site (i.e. annulus). Again, this is preferably accomplished while employing the nerve detection and/or direction features described above. After the initial dilating assembly 40 is advanced such that the distal ends of the split-dilator 48 and initial dilator 44 are positioned within the disc space (FIG. 2), the initial dilator 44 and handle 46 are removed (FIG. 3) to thereby leave the split-dilator 48 and K-wire 42 in place. As shown in FIG. 4, the split-dilator 48 is thereafter split such that the respective halves 48a, 48b are separated from one another to distract tissue in a generally cephalad-caudal fashion relative to the target site. The split dilator 48 may thereafter be relaxed (allowing the dilator halves 48a, 48b to come together) and rotated such that the dilator halves 48a, 48b are disposed in the anterior-posterior plane. Once rotated in this manner, the dilator halves 48a, 48b are again separated to distract tissue in a generally anterior-posterior fashion. Each dilator halve 48a, 48b may be, according to the present invention, provided with one or more electrodes (preferably at their distal regions) equipped for use with a nerve surveillance system, such as, by way of example, the type shown and described in the NeuroVision PCT Applications.

Figure 5:
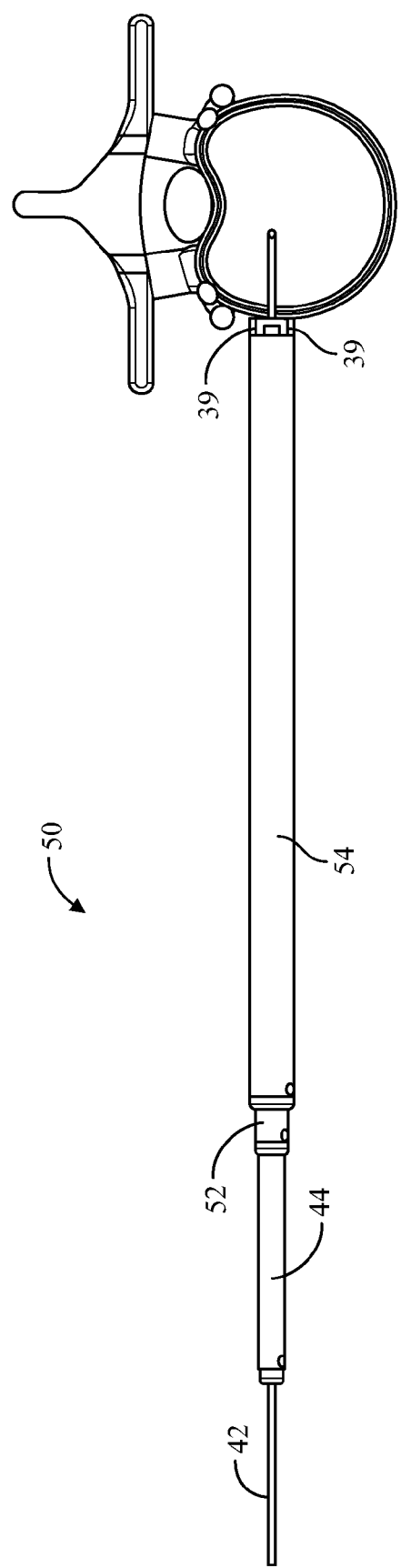
FIG. 5 is a side view illustrating the use of a secondary distraction assembly (comprising a plurality of dilating cannulae over the K-wire) to further distract tissue between the skin of the patient and the surgical target site according to the present invention.

Following this initial distraction, a secondary distraction may be optionally undertaken, such as via a sequential dilation system 50 as shown in FIG. 5. According to the present invention, the sequential dilation system 50 may include the K-wire 42, the initial dilator 44, and one or more supplemental dilators 52, 54 for the purpose of further dilating the tissue down to the surgical target site. Once again, each component of the secondary distraction assembly 50 (namely, the K-wire 42, the initial dilator 44, and the supplemental dilators 52, 54) may be, according to the present invention, provided with one or more electrodes (preferably at their distal regions) equipped for use with a nerve surveillance system, such as, by way of example, the type shown and described in the NeuroVision PCT Applications.

Figure 6:
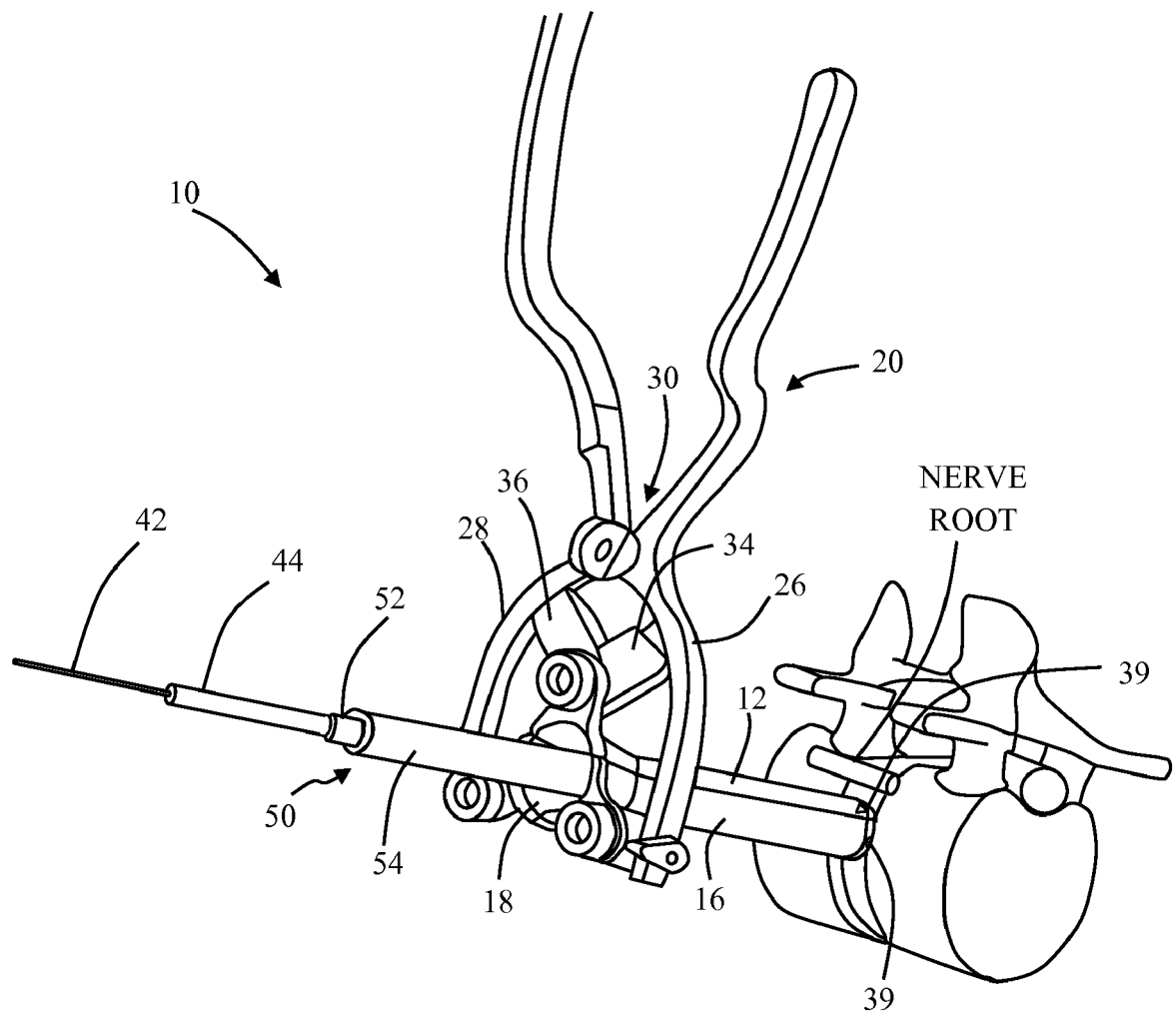
FIG. 6 is a perspective view of a retractor assembly according to the present invention, comprising a linkage assembly having three (3) retractor blades coupled thereto (posterior, cephalad, and caudal) for the purpose of creating an operative corridor to the surgical target site (shown in a first, closed position)
Figure 7:
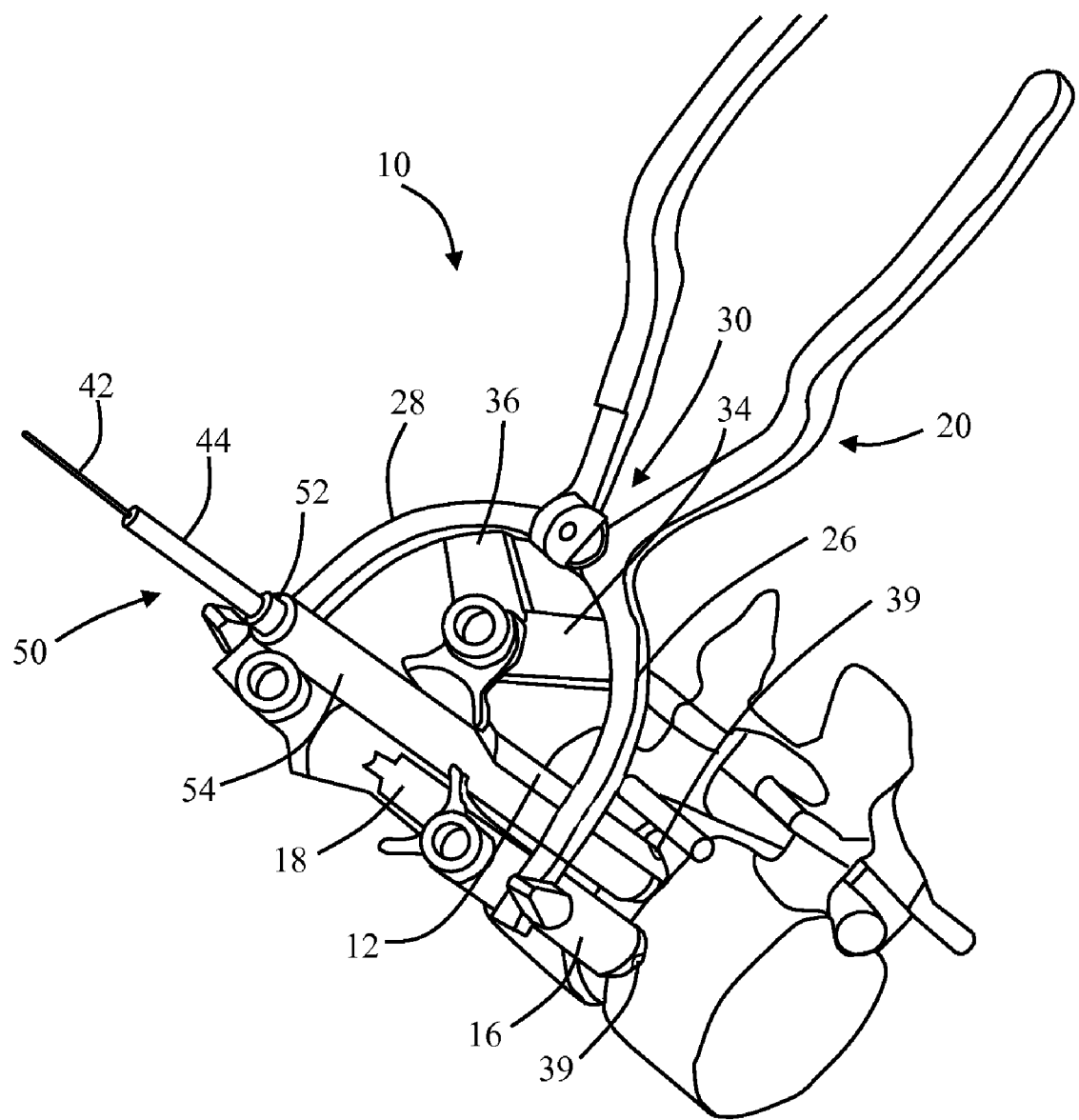
FIG. 7 is a perspective view of the retractor assembly of FIG. 6 in a second, opened (i.e. retracted) position according to the present invention.

As shown in FIG. 6, the retraction assembly 10 of the present invention is thereafter advanced along the exterior of the sequential dilation system 50. This is accomplished by maintaining the retractor blades 12-16 in a first, closed position (with the retractor blades 12-16 in generally abutting relation to one another). Once advanced to the surgical target site, the linkage assembly 20 may be operated as shown in FIG. 7 to move the retractor blades 12-16 into a second, open or "retracted" position. As one can see, the posterior retractor blade 12 is allowed to stay in the same general position during this process, such that the cephalad and caudal retractor blades 14, 16 move away from the posterior retractor blade 12. Again, this is accomplished through the use of the pivot linkage 32 between the posterior retractor blade 12 and the arms 26, 28 of the linkage assembly 20.

Figure 8:
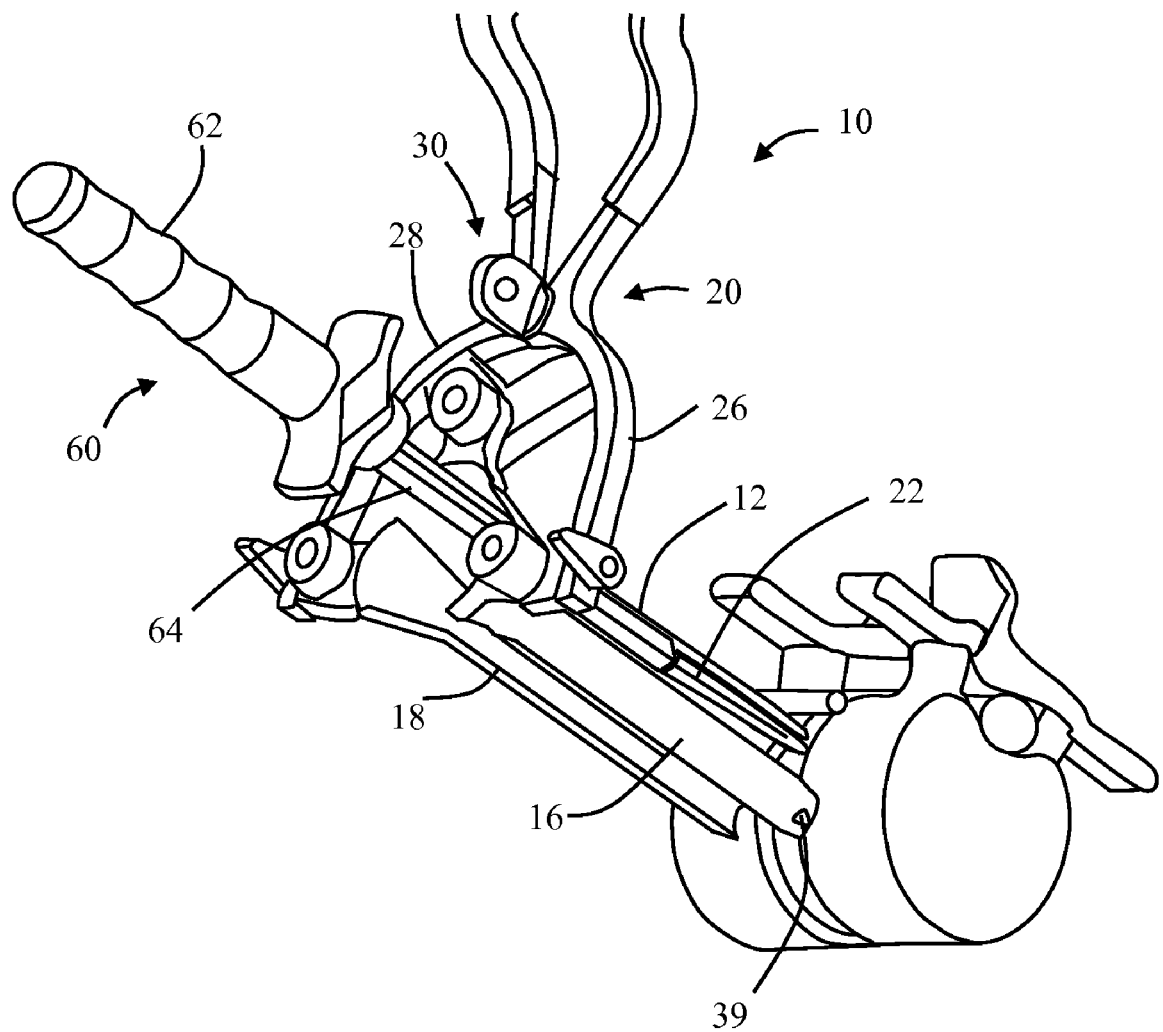
FIG. 8 is a perspective view illustrating a shim introducer introducing a shim element along the interior of the posterior retractor blade such that a distal portion (shim extension) is positioned within the disc space.
Figure 10:
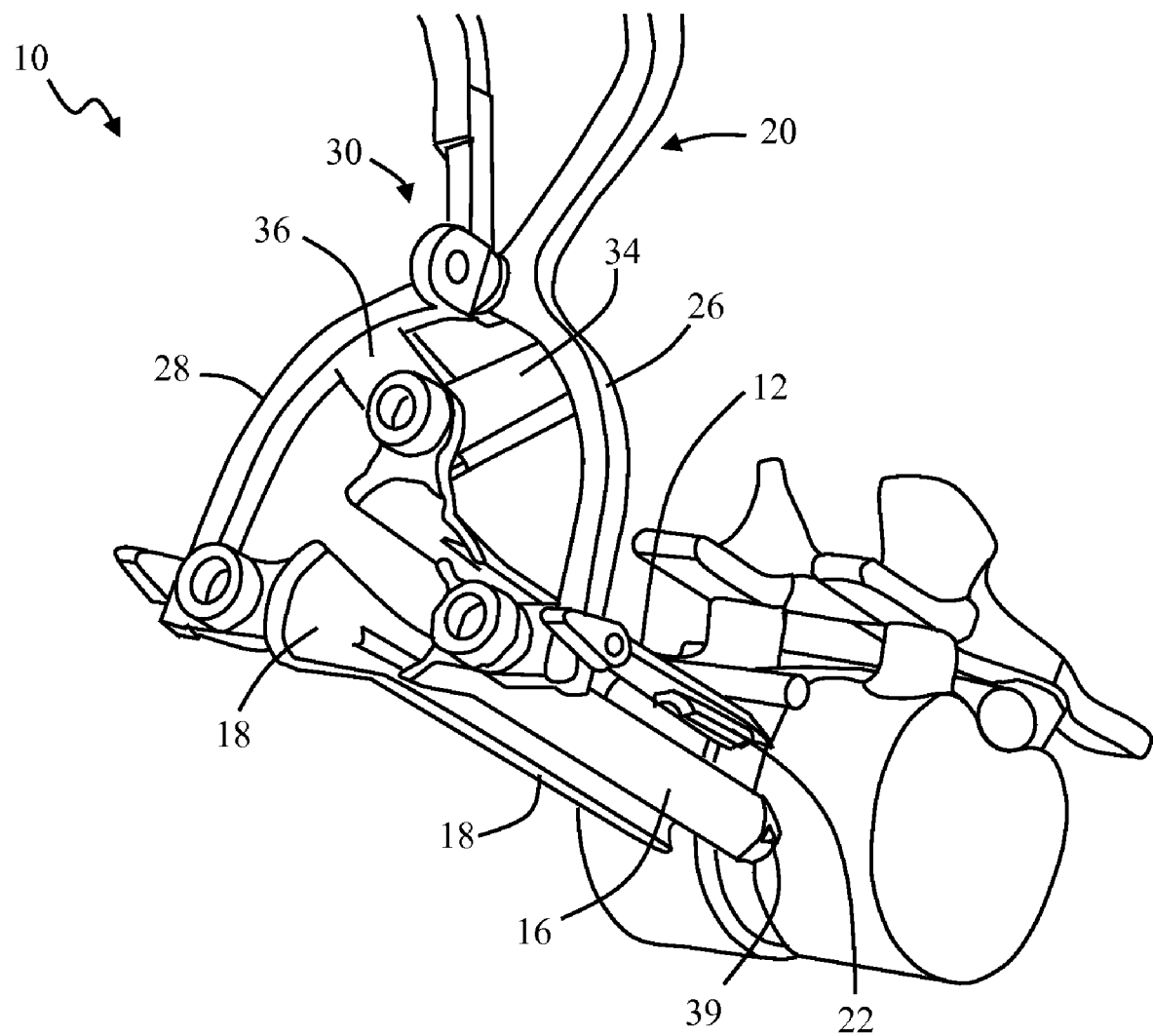
FIG. 10 is a perspective view of the retractor assembly of the present invention with the shim element disposed along the posterior retractor blade according to the present invention.
Figure 11:
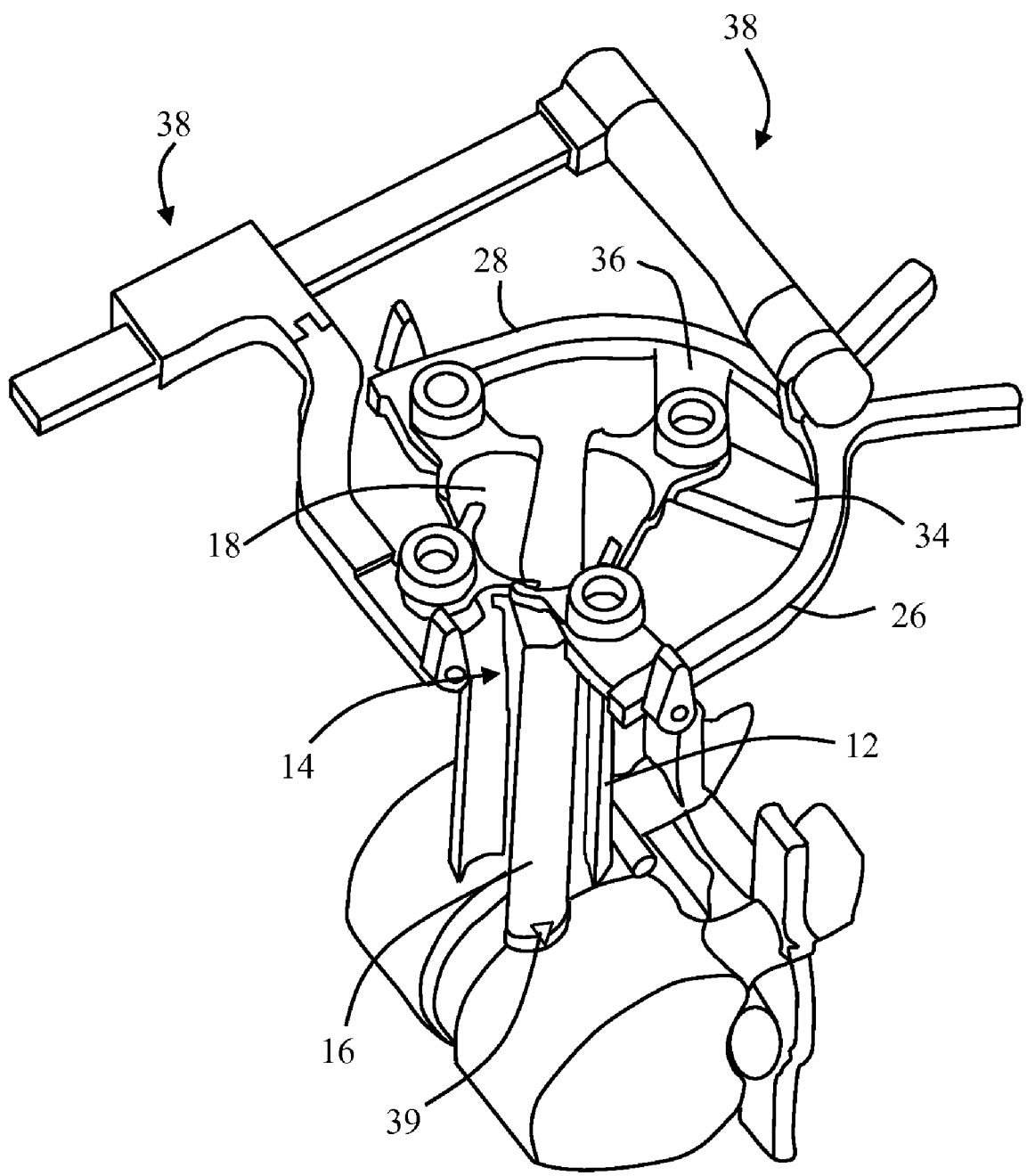
FIGS. 11-12 are perspective views of the retractor assembly of the present invention, wherein an anterior retractor blade is provided coupled to the linkage assembly via an arm assembly.
Figure 12:
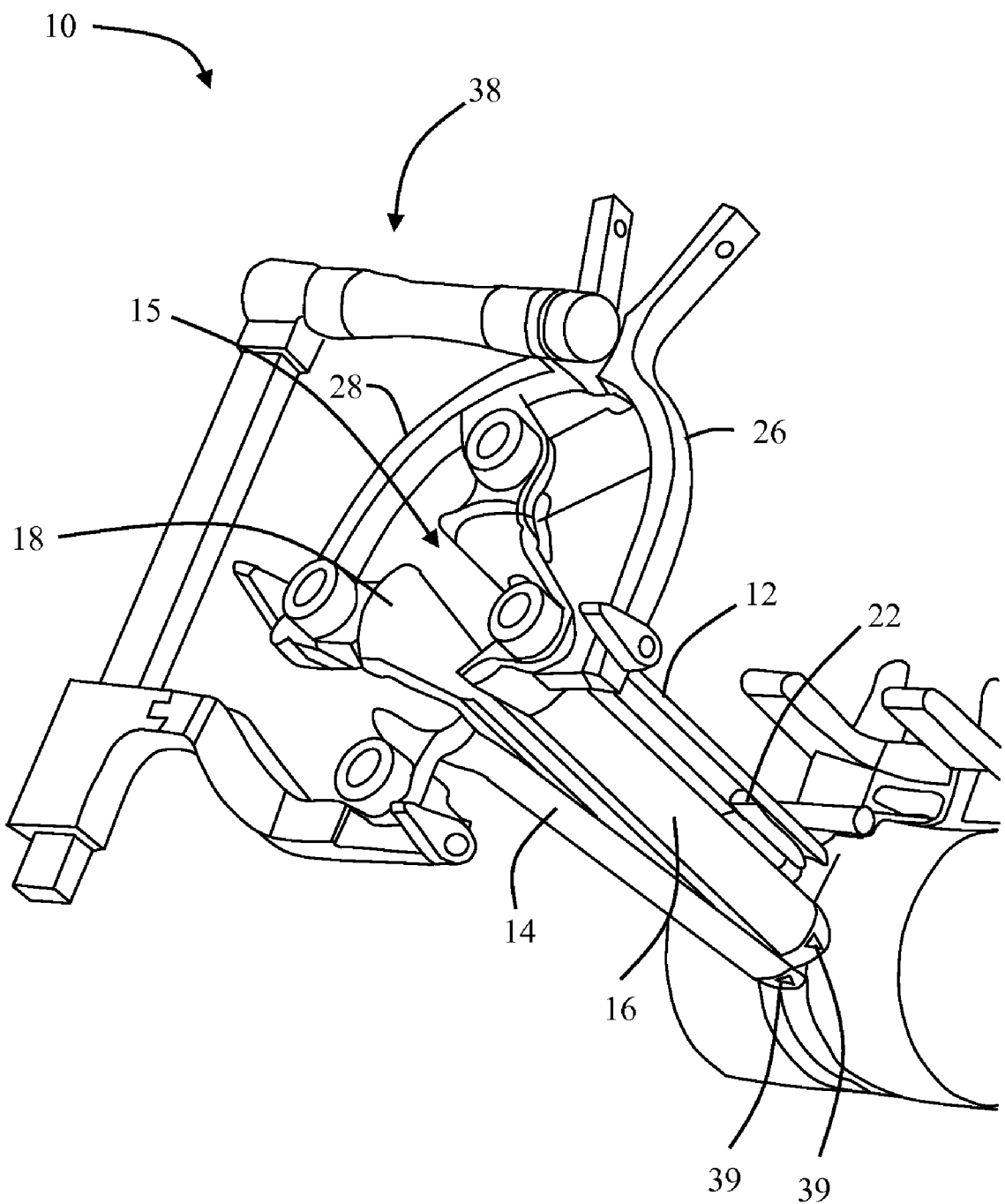
Figure 13:
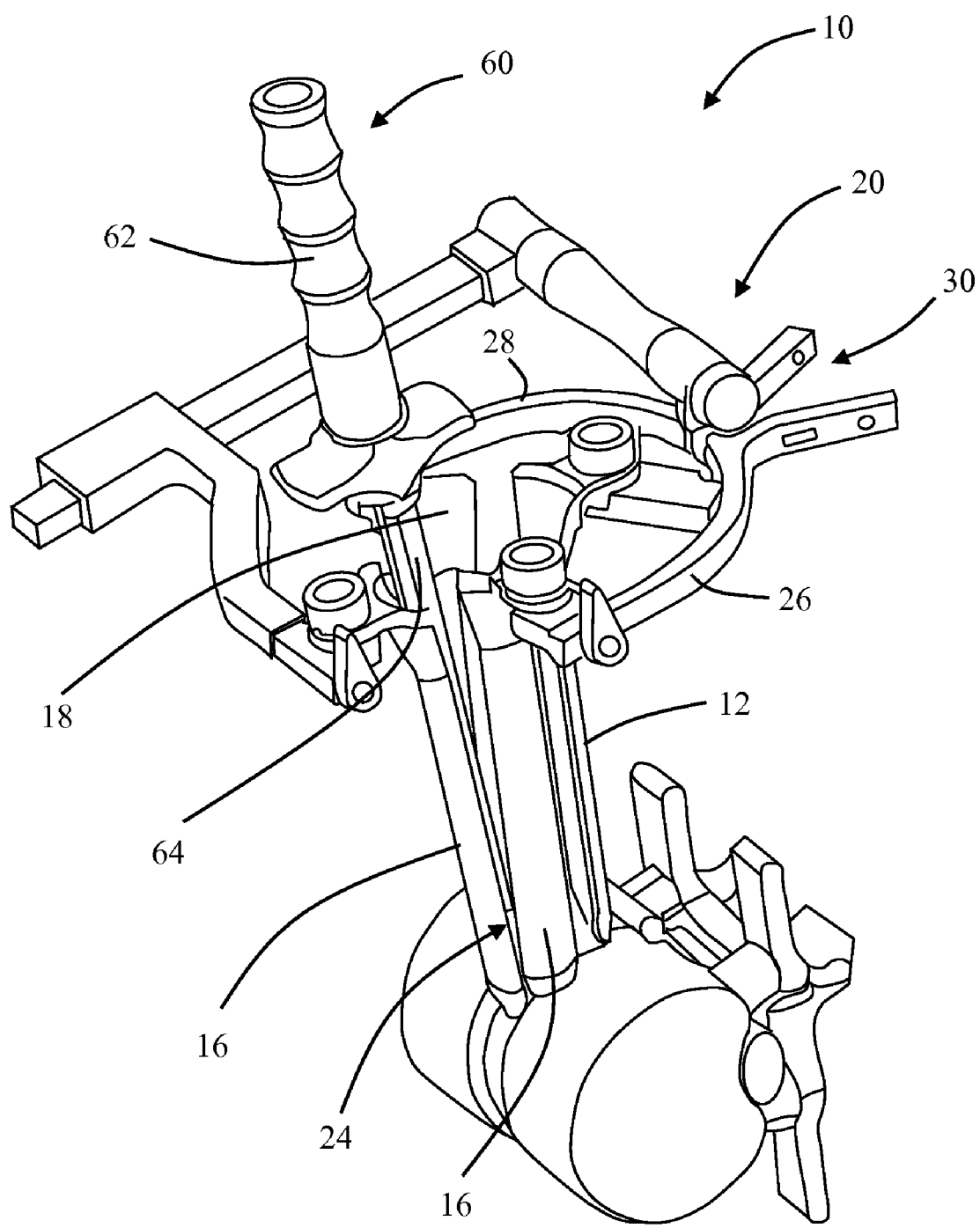
FIG. 13 is a perspective view of the retractor assembly of the present invention wherein a shim introducer is employed to introducer a shim along the anterior retractor blade according to the present invention.
Figure 14:
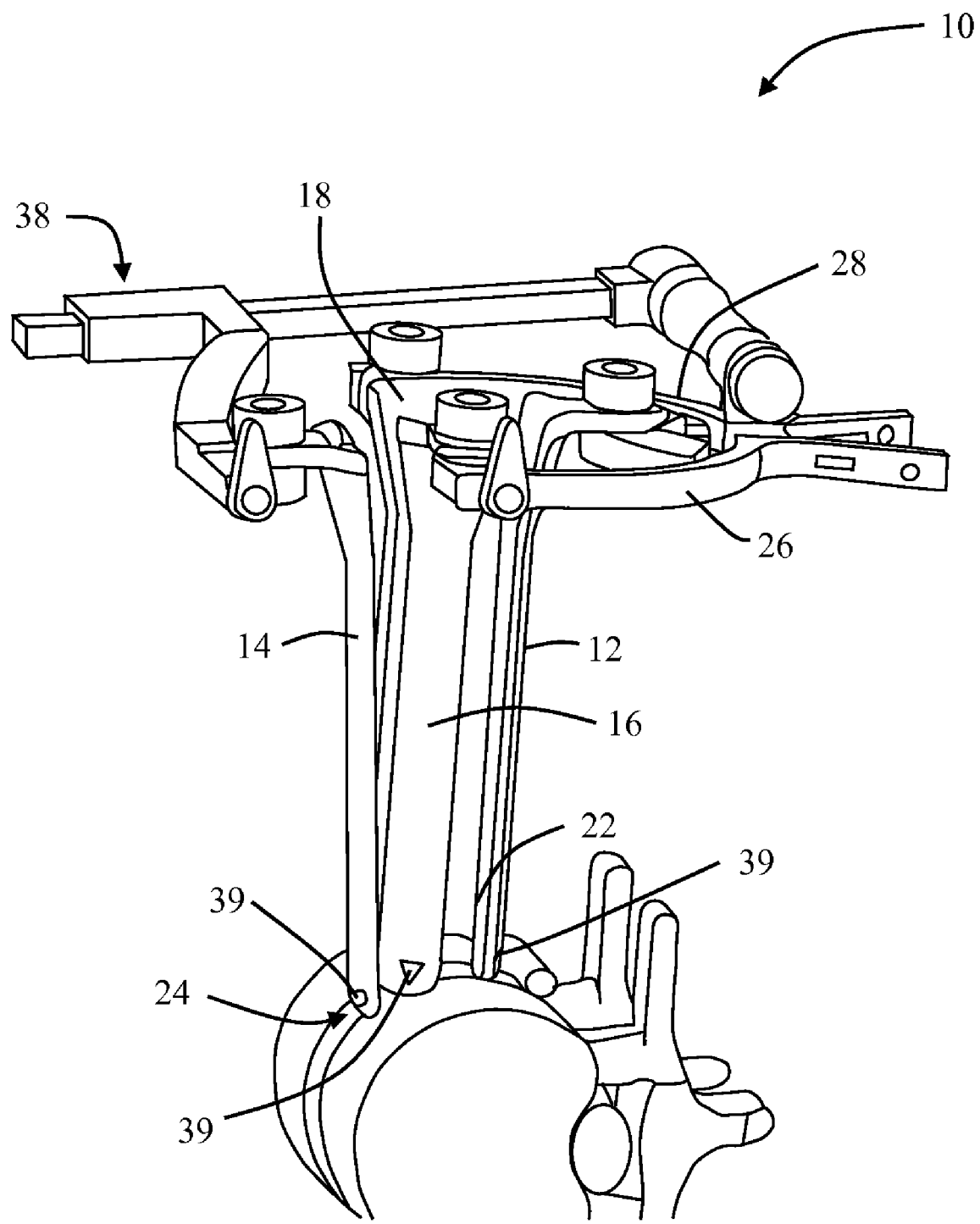
FIG. 14 is a perspective view of the retractor assembly of the present invention, wherein the anterior retractor blade may be positioned at a different vertical level than the posterior, cephalad, and caudal retractor blades according to the present invention.

At this point, as shown in FIG. 8, the posterior shim element 22 (FIG. 9) may be advanced along an engagement slot formed along the interior surface of the posterior retractor blade 12 such that the shim extension (distal end) is positioned in the posterior region of the disc space as shown in FIG. 10. To aid in this process, a shim introducer 60 may be provided, which includes a handle member 62 and an elongate portion 64 capable of delivering the shim element 22 along the interior of the posterior retractor blade 12 and thereafter selectively disengaging the shim element 22 so as to remove the elongate portion 64 from the operative site. As shown in FIGS. 11-12, the anterior retractor blade 14 may thereafter be positioned relative to the posterior, cephalad, and caudal retractor blades 12, 16, 18, respectively, by virtue of the arm assembly 38. The anterior shim element 24 may thereafter be advanced along the anterior retractor blade 14 such that the shim extension (distal region thereof) extends into the anterior region of the disc space as shown in FIG. 13. The end result is shown in FIG. 14, with the retraction assembly 10 of the present invention disposed in position over a surgical target site.

Figure 15:
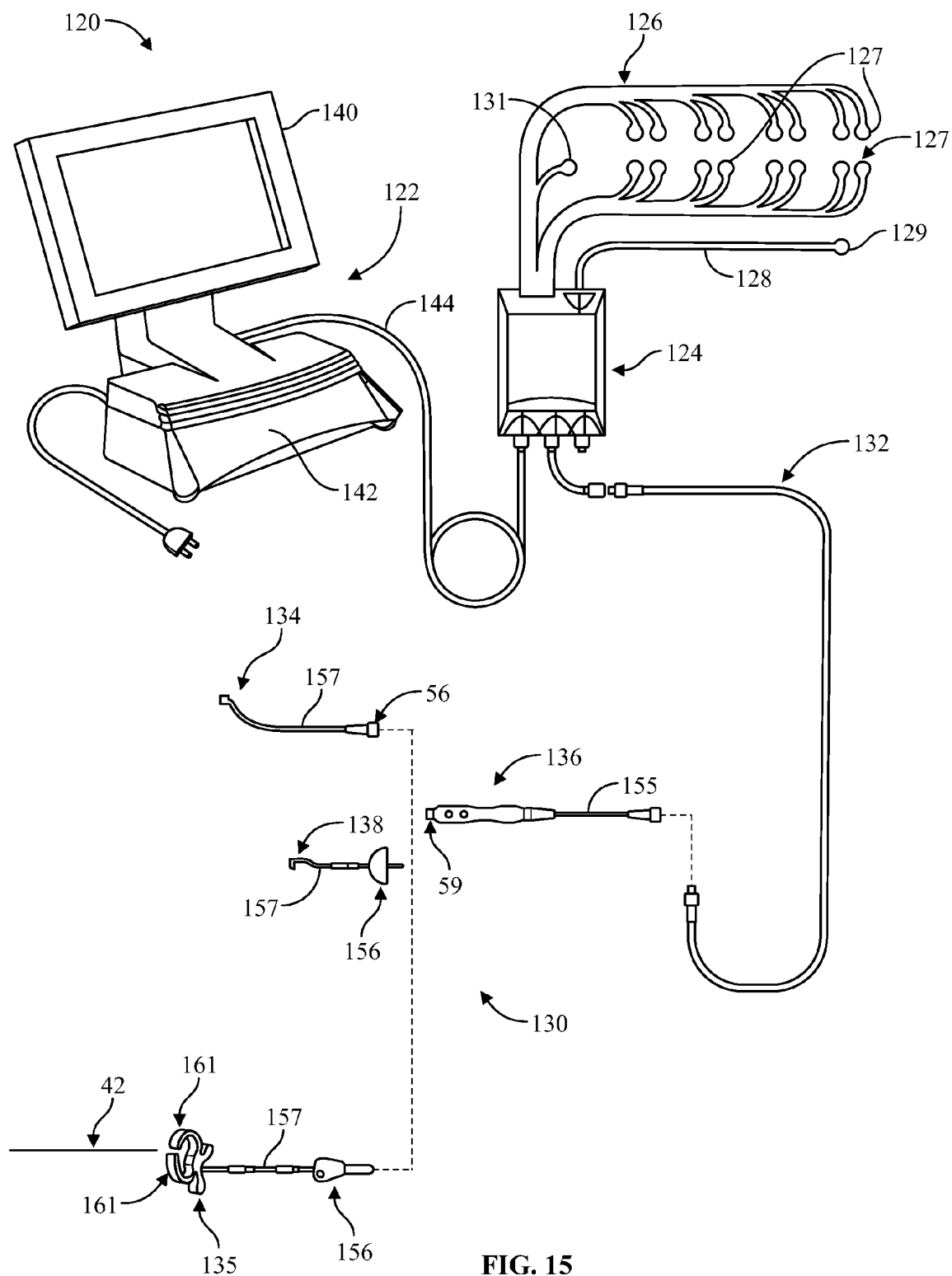
FIG. 15 is a perspective view of an exemplary nerve monitoring system capable of performing nerve monitoring before, during and after the creating of an operative corridor to a surgical target site using the surgical access system in accordance with the present invention.
Figure 16:
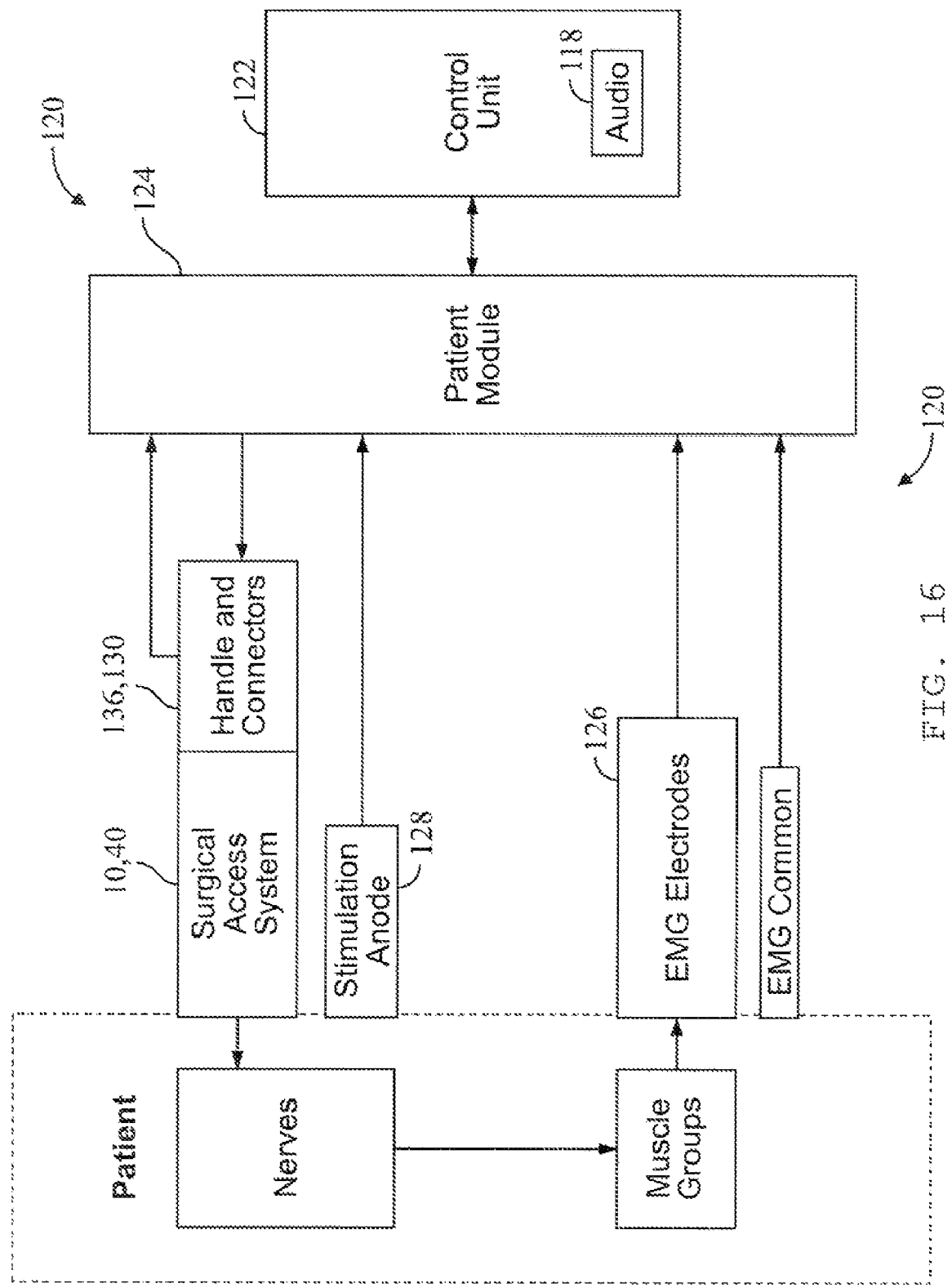
FIG. 16 is a block diagram of the nerve monitoring system shown in FIG. 15.

FIGS. 15-16 illustrate, by way of example only, a surgical system 120 provided in accordance with a broad aspect of the present invention. The surgical system 120 includes a control unit 122, a patient module 124, an EMG harness 126 and return electrode 128 coupled to the patient module 124, and an accessory cable 132 in combination with a handle assembly 136. The handle assembly 136 includes one or more electrical connectors 130, including (by way of example only) a pin connector 134, a pin connector 138, and a clamping-style connector 135. As shown in dotted lines, each of the electrical connectors 130 may be coupled to the handle assembly 136 and include a manner of establishing electrical communications with any of the electrodes 39 provided on the distraction and/or retraction assemblies of the present invention, including the shims 22, 24 (collectively "Surgical Access Instruments"). By establishing electrical communication in this fashion, the handle assembly 136 may be employed to selectively apply a stimulation signal to any of the Surgical Access Instruments to detect the presence of (and optionally direction to) neural structures during and/or after the distraction and retraction steps of the present invention.

The control unit 122 includes a touch screen display 140 and a base 142, which collectively contain the essential processing capabilities for controlling the surgical system 120. The patient module 124 is connected to the control unit 122 via a data cable 144, which establishes the electrical connections and communications (digital and/or analog) between the control unit 122 and patient module 124. The main functions of the control unit 122 include receiving user commands via the touch screen display 140, activating stimulation, processing signal data according to defined algorithms (described below), displaying received parameters and processed data, and monitoring system status and reporting fault conditions. The touch screen display 140 is preferably equipped with a graphical user interface (GUI) capable of communicating information to the user and receiving instructions from the user. The display 140 and/or base 142 may contain patient module interface circuitry that commands the stimulation sources, receives digitized signals and other information from the patient module 124, processes the EMG responses to extract characteristic information for each muscle group, and displays the processed data to the operator via the display 140.

The accessory handle assembly 136 includes a cable 155 for establishing electrical communication with the patient module 124 (via the accessory cable 132). In a preferred embodiment, each electrical connector 130 includes a proximal electrical connector 156 and an electrical cable 157 for establishing electrical communication between the handle assembly 136 and the electrical connectors 134, 138, and 135. The proximal electrical connector 156 may be designed to thread and/or snap into engagement with the distal end 159 of the handle assembly 136. In this fashion, the Surgical Access Instruments may be quickly and easily coupled (electrically and mechanically) to the accessory handle assembly 136. The pin connectors 134 and 138 may be designed to engage with electrical mating portions provided on the Surgical Access Instruments, wherein these electrical mating portions are in turn electrically coupled to the electrodes 39. The distal electrical connector of the clamp-type coupler 135 may include any number of suitable electrode or electrode regions (including protrusions) on or about the distal (or pinching) ends of the clamp arms 161 forming the coupler 135. Corresponding regions (such as electrodes or electrode regions—including indentations) may be provided on the Surgical Access Instruments (including K-wire 42) according to the present invention.

In all situations, the user may operate one or more buttons of the handle assembly 136 to selectively initiate a stimulation signal (preferably, a current signal) from the patient module 124 to one of the electrical connectors 130, and hence the electrodes 39 on the distraction and retraction assemblies of the present invention. By monitoring the myotomes associated with the nerve roots (via the EMG harness 126 and recording electrode 127) and assessing the resulting EMG responses (via the control unit 122), the surgical system 120 can detect the presence of (and optionally the direction to) neural structures during and after the distraction and/or retraction according to the present invention.

In one embodiment, the monitoring system 120 is capable of determining nerve presence and/or direction relative to one or more of the K-wire 42, dilating cannula 44, split-retractor 48, retractor blades 12-18, and/or the shim elements 22, 24 before, during and/or following the creation of an operative corridor to a surgical target site. Monitoring system 120 accomplishes this by having the control unit 122 and patient module 124 cooperate to send electrical stimulation signals to one or more of the stimulation electrodes provided on these Surgical Access Instruments. Depending upon the location within a patient (and more particularly, to any neural structures), the stimulation signals may cause nerves adjacent to or in the general proximity of the Surgical Access Instruments to depolarize. This causes muscle groups to innervate and generate EMG responses, which can be sensed via the EMG harness 126. The nerve direction feature of the system 120 is based on assessing the evoked response of the various muscle myotomes monitored by the system 120 via the EMG harness 126.

By monitoring the myotomes associated with the nerves (via the EMG harness 126 and recording electrode 127) and assessing the resulting EMG responses (via the control unit 122), the surgical access system of the present invention is capable of detecting the presence of (and optionally the distant and/or direction to) such nerves. This provides the ability to actively negotiate around or past such nerves to safely and reproducibly form the operative corridor to a particular surgical target site, as well as monitor to ensure that no neural structures migrate into contact with the retraction assembly 10 after the operative corridor has been established. In spinal surgery, for example, this is particularly advantageous in that the surgical access system of the present invention may be particularly suited for establishing an operative corridor to an intervertebral target site in a postero-lateral, trans-psoas fashion so as to avoid the bony posterior elements of the spinal column.

Figure 17:
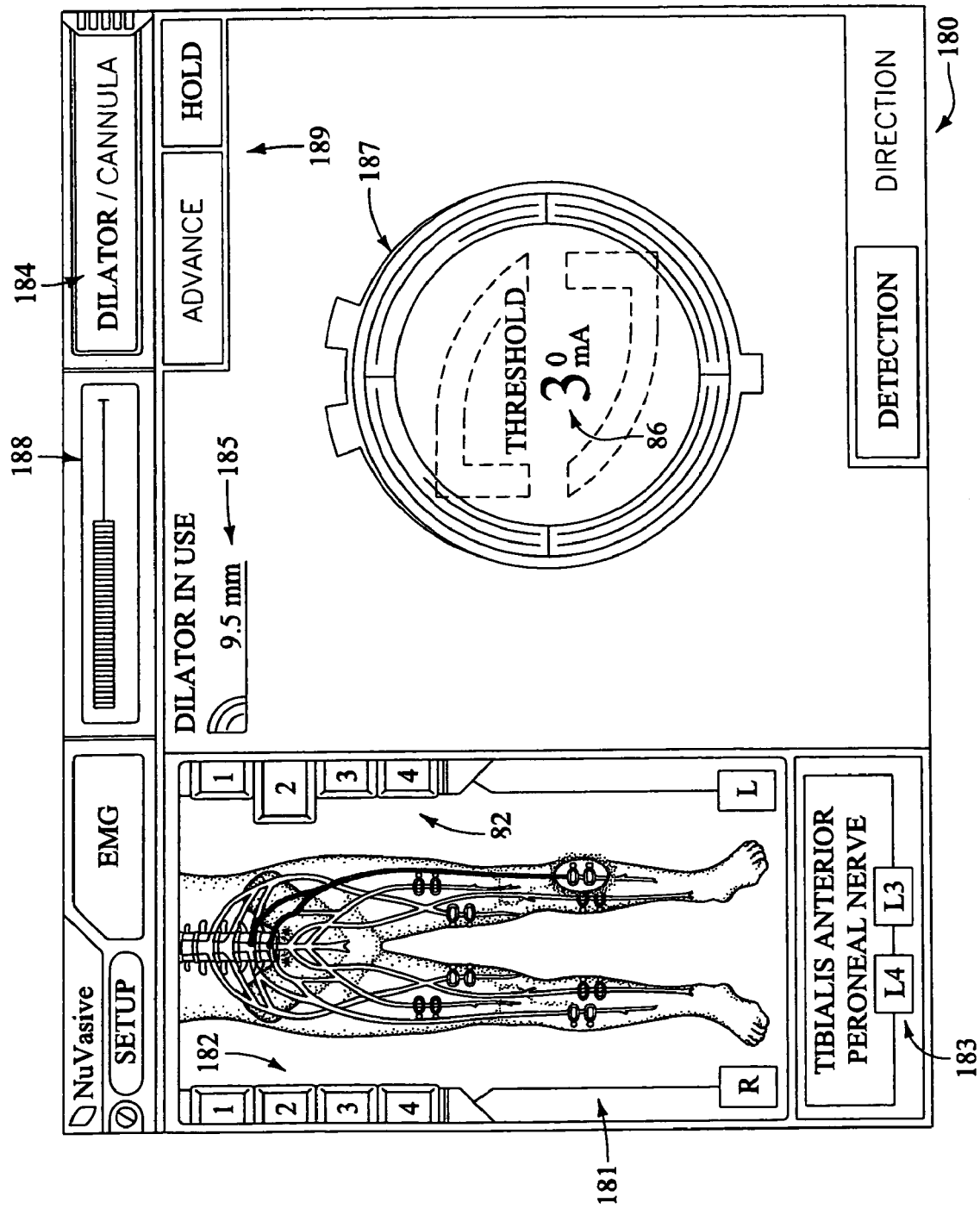
FIGS. 17-18 are screen displays illustrating exemplary features and information communicated to a user during the use of the nerve monitoring system of FIG. 15.
Figure 18:
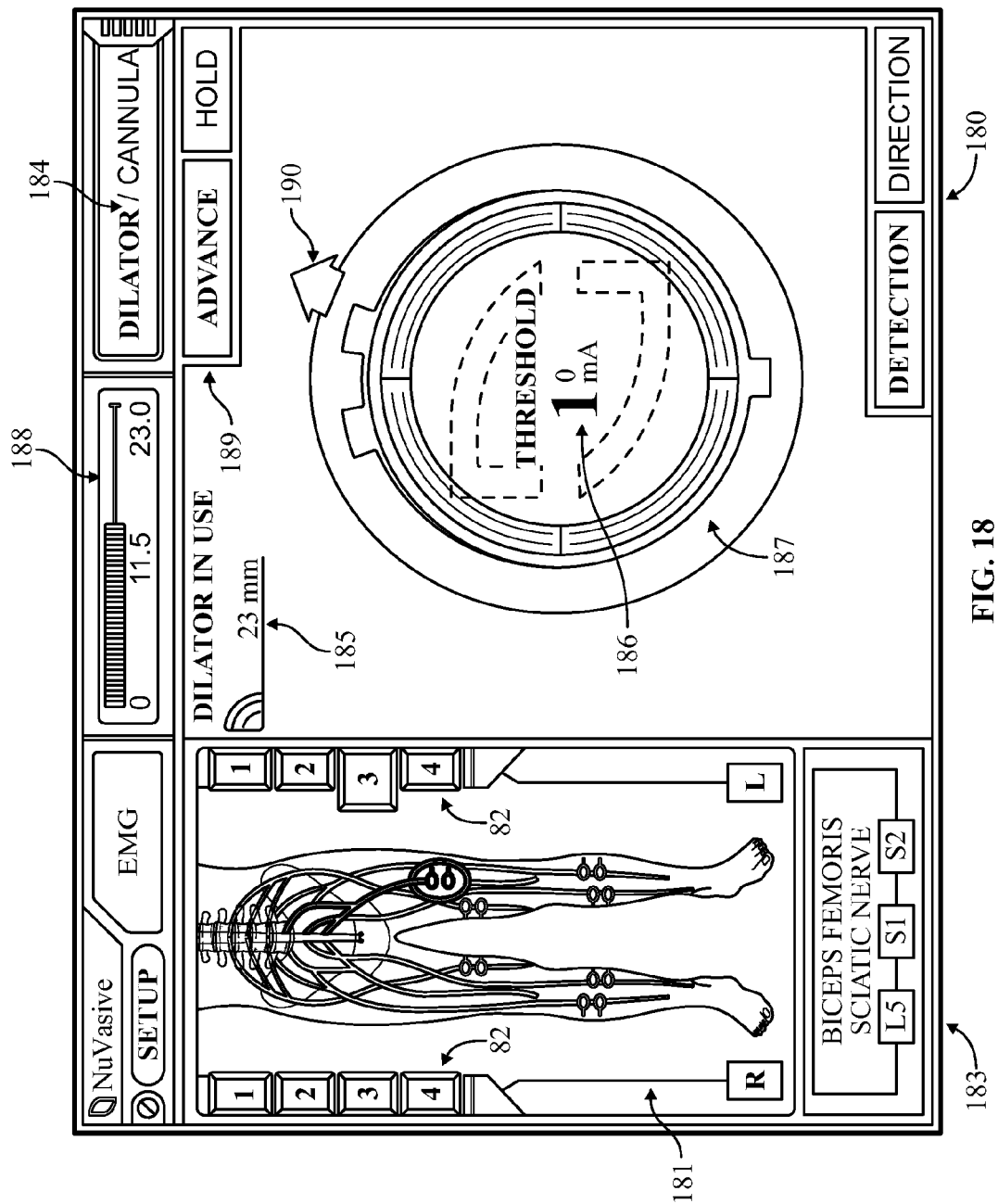

FIGS. 17-18 are exemplary screen displays (to be shown on the display 140) illustrating one embodiment of the nerve direction feature of the monitoring system shown and described with reference to FIGS. 15-16. These screen displays are intended to communicate a variety of information to the surgeon in an easy-to-interpret fashion. This information may include, but is not necessarily limited to, a display of the function 180 (in this case "DIRECTION"), a graphical representation of a patient 181, the myotome levels being monitored 182, the nerve or group associated with a displayed myotome 183, the name of the instrument being used 184 (e.g. dilating cannula 44), the size of the instrument being used 185, the stimulation threshold current 186, a graphical representation of the instrument being used 187 (in this case, a cross-sectional view of a dilating cannula 44) to provide a reference point from which to illustrate relative direction of the instrument to the nerve, the stimulation current being applied to the stimulation electrodes 188, instructions for the user 189 (in this case, "ADVANCE" and/or "HOLD"), and (in FIG. 19) an arrow 190 indicating the direction from the instrument to a nerve. This information may be communicated in any number of suitable fashions, including but not limited to the use of visual indicia (such as alpha-numeric characters, light-emitting elements, and/or graphics) and audio communications (such as a speaker element). Although shown with specific reference to a dilating cannula (such as at 184), it is to be readily appreciated that the present invention is deemed to include providing similar information on the display 140 during the use of any or all of the various Surgical Access Instruments of the present invention, including the initial distraction assembly 40 (i.e. the K-wire 42, dilating cannula 44, and split dilator 48), the secondary distraction assembly 50, and/or the retractor blades 12-18 and/or shim elements 22, 24 of the refraction assembly 10.

The retractor blades 12-18 and the shim elements 22, 24 of the present invention may also be provided with one or more electrodes for use in providing the neural monitoring capabilities of the present invention. By way of example only, it may be advantageous to provide one or more electrodes on these components (preferably on the side facing away from the surgical target site) for the purpose of conducting neural monitoring before, during and/or after the retractor blades 12-18 and/or shim elements 22, 24 have been positioned at or near the surgical target site.

The surgical access system of the present invention may be sold or distributed to end users in any number of suitable kits or packages (sterile and/or non-sterile) containing some or all of the various components described herein. For example, the retraction assembly 10 may be provided such that the mounting assembly 20 is reusable (e.g., autoclavable), while the retractor blades 12-18 and/or shim elements 22, 24 are disposable. In a further embodiment, an initial kit may include these materials, including a variety of sets of retractor blades 12-18 and/or shim elements 22, 24 (and extensions 80) having varying (or "incremental") lengths to account for surgical target sites of varying locations within the patient, optionally color-coded to designate a predetermined length.

As evident from the above discussion and drawings, the present invention accomplishes the goal of providing a novel surgical access system and related methods which involve creating a distraction corridor to a surgical target site, thereafter retracting the distraction corridor to establish and maintain an operative corridor to the surgical target site, and optionally detecting the existence of (and optionally the distance and/or direction to) neural structures before, during and/or after the formation of the distraction and/or operative corridors.

The surgical access system of the present invention can be used in any of a wide variety of surgical or medical applications, above and beyond the spinal applications discussed herein. By way of example only, in spinal applications, any number of implants and/or instruments may be introduced through the operative corridor, including but not limited to spinal fusion constructs (such as allograft implants, ceramic implants, cages, mesh, etc.), fixation devices (such as pedicle and/or facet screws and related tension bands or rod systems), and any number of motion-preserving devices (including but not limited to nucleus replacement and/or total disc replacement systems).

While certain embodiments have been described, it will be appreciated by those skilled in the art that variations may be accomplished in view of these teachings without deviating from the spirit or scope of the present application. For example, with regard to the monitoring system 120, it may be implemented using any combination of computer programming software, firmware or hardware. As a preparatory act to practicing the system 120 or constructing an apparatus according to the application, the computer programming code (whether software or firmware) according to the application will typically be stored in one or more machine readable storage mediums such as fixed (hard) drives, diskettes, optical disks, magnetic tape, semiconductor memories such as ROMs, PROMs, etc., thereby making an article of manufacture in accordance with the application. The article of manufacture containing the computer programming code may be used by either executing the code directly from the storage device, by copying the code from the storage device into another storage device such as a hard disk, RAM, etc. or by transmitting the code on a network for remote execution. As can be envisioned by one of skill in the art, many different combinations of the above may be used and accordingly the present application is not limited by the scope of the appended claims.

What is claimed is:

1. A system for forming an operating corridor to a lumbar spine, comprising:
    an elongate member deliverable to a spinal disc along a lateral, trans-psoas path to the lumbar spine such that a distal tip region of the elongate member engages an annulus of the spinal disc, the distal tip region of the elongate member including a stimulation electrode to deliver electrical stimulation for nerve monitoring when the elongate member is positioned in the lateral, trans-psoas path;
    a dilator system to create a distraction corridor along the lateral, trans-psoas path to the lumbar spine, the dilator system comprising a dilator that slidably engages an exterior of the elongate member, the dilator being deliverable to the spinal disc along the lateral, trans-psoas path to the lumbar spine;
    a three-bladed retractor assembly slidable over the dilator system toward the spinal disc along the lateral, trans-psoas path, the three-bladed retractor assembly including:
        a blade holder assembly and first, second, and third retractor blades that extend generally perpendicularly relative to arm portions of the blade holder assembly, the first, second, and third retractor blades each having a concave surface region along an inner facing distal end portion,
        wherein the three-bladed retractor assembly is adjustable from a first position in which the first, second, and third retractor blades are slidable over the dilator system to a second position in which the second and third retractor blades are positioned away from the first retractor blade to enlarge the distraction corridor and thereby form an operative corridor along the lateral, trans-psoas path to the lumbar spine, and
        wherein the second and third retractor blades are movable relative to the first blade in response to pivoting movement of two of the arm portions of the blade holder assembly,
        a posterior shim element to releasably engage with a posterior-most retractor blade of the first, second, and third retractor blades so that a portion of the posterior shim element extends distally from the posterior-most retractor blade to anchor into the spinal disc; and
    wherein when the three-bladed retractor assembly is adjusted to the second position to form the operative corridor along the lateral, trans-psoas path to the lumbar spine, the first retractor blade is the posterior-most retractor blade of the first, second, and third retractor blades and the operative corridor is dimensioned so as to pass an implant through the operative corridor along the lateral, trans-psoas path to the lumbar spine.

2. The system of claim 1, wherein when the three-bladed retractor assembly is adjusted to the second position to form the operative corridor, the first retractor blade is the posterior-most retractor blade, the second blade is a cephalad-most retractor blade, and the third blade is a caudal-most retractor blade.

3. The system of claim 2, wherein when the three-bladed retractor assembly is adjusted to the second position to form the operative corridor, the cephalad-most retractor blade and the caudal-most retractor blade are moved away from one another and the posterior shim element is releasably engaged with the posterior-most retractor blade.

4. The system of claim 2, wherein when the three-bladed retractor assembly is adjusted to the second position to form the operative corridor, the cephalad-most retractor blade and the caudal-most retractor blade are moved away from one another and a fourth retractor blade is positioned anterior to the cephalad-most retractor blade and the caudal-most retractor blade.

5. The system of clam 1, wherein the posterior shim element is slidable along an engagement slot defined along an inner face of the posterior-most retractor blade.

6. The system of claim 5, wherein the posterior shim element comprises a rearward protrusion to engage with the engagement slot along the inner face of the posterior-most retractor blade.

7. The system of claim 1, wherein the posterior shim element comprises a distal portion to penetrate into the spinal disc, the distal portion of the posterior shim element having a width that is less than a proximal portion of the posterior shim element, and the posterior shim element comprises a rearwardly extending tab to engage with the posterior-most retractor blade.

8. The system of claim 7, wherein the distal portion of posterior shim element has a smallest width at a rounded distal tip.

9. The system of claim 1, wherein when the three-bladed retractor assembly is adjusted to the second position to form the operative corridor along the lateral, trans-psoas path, a distal portion of the posterior shim element is configured to anchor in the spinal disc to secure the posterior-most retractor blade in fixed relation relative to the lumbar spine.

10. The system of claim 1, further comprising a fourth retractor blade that couples with the blade holder assembly of the three-bladed retractor assembly.

11. The system of claim 10, wherein the fourth retractor blade releasably couples with the blade holder assembly so that the fourth retractor blade is an anterior-most retractor blade.

12. The system of claim 1, wherein the elongated member is advanced together with the dilator along the lateral, trans-psoas path to the lumbar spine.

13. The system of claim 1, wherein when the three-bladed retractor assembly is in the first position, the first, second, and third retractor blades are adjacent to one another.

14. The system of claim 13, wherein when the three-bladed retractor assembly is in the first position, each of the first, second, and third retractor blades are in generally abutting relation with the other two of the first, second, and third retractor blades.

15. The system of claim 1, wherein the dilator system comprises a plurality of supplemental dilators for sequential insertion along the lateral, trans-psoas path to the lumbar spine.

16. The system of claim 15, wherein each of the plurality of supplemental dilators comprises a stimulation electrode to deliver electrical stimulation for nerve monitoring.

17. The system of claim 1, wherein the elongate member comprises a K-wire.

18. A system for forming an operating corridor to a lumbar spine, comprising:
an elongate member deliverable to a spinal disc along a lateral, trans-psoas path to the lumbar spine such that a distal tip region of the elongate member engages an annulus of the spinal disc, the distal tip region of the elongate member including a stimulation electrode to deliver electrical stimulation for nerve monitoring when the elongate member is positioned in the lateral, trans-psoas path;
a dilator system to create a distraction corridor along the lateral, trans-psoas path to the lumbar spine, the dilator system comprising a dilator that slidably engages an exterior of the elongate member, the dilator being deliverable to the spinal disc along the lateral, trans-psoas path to the lumbar spine;
a three-bladed retractor assembly slidable over the dilator system toward the spinal disc along the lateral, trans-psoas path, the three-bladed retractor assembly including:
a blade holder assembly and first, second, and third retractor blades that extend generally perpendicularly relative to arm portions of the blade holder assembly, wherein the three-bladed retractor assembly is adjustable from a first position in which the first, second, and third retractor blades are slidable over the dilator system to a second position in which the second and third retractor blades are positioned away from the first retractor blade to enlarge the distraction corridor and thereby form an operative corridor along the lateral, trans-psoas path to the lumbar spine, and
wherein the second and third retractor blades are movable relative to the first blade in response to pivoting movement of two of the arm portions of the blade holder assembly,
a posterior shim element to releasably engage with a posterior-most retractor blade of the first, second, and third retractor blades so that a portion of the posterior shim element extends distally from the posterior-most retractor blade to anchor into the spinal disc; and
wherein when the three-bladed retractor assembly is adjusted to the second position to form the operative corridor along the lateral, trans-psoas path to the lumbar spine, the first retractor blade is the posterior-most retractor blade of the first, second, and third retractor blades and the operative corridor is dimensioned so as to pass an implant through the operative corridor along the lateral, trans-psoas path to the lumbar spine; and
a monitoring system that is configured to deliver an electrical stimulation signal to the stimulation electrode of the elongate member, configured to monitor electromyographic activity detected by a set of sensor electrodes in leg muscle myotomes associated with nerves in the vicinity of the spinal disc, and configured to display to a user: a numeric stimulation threshold required to obtain the electromyographic activity in at least one of said leg muscle myotomes, and myotomes levels being monitored.

19. The system of claim 18, wherein the monitoring system comprises a control unit having a video display device, a patient module connected to the control unit via a data cable, an EMG sensor harness having the set of sensor electrodes connected to the patient module.

20. The system of claim 19, wherein the control unit receives signals from the patient module and processes EMG responses output from the sensor electrodes to extract characteristic information for each of said leg muscle myotomes.

21. A system for forming an operating corridor to a lumbar spine, comprising:
- a dilator system to create a distraction corridor to a spinal disc along a lateral, trans-psoas path to the lumbar spine, the dilator system comprising: a plurality of sequential dilators including an initial dilator having a distal stimulation electrode to deliver electrical stimulation for nerve monitoring when the initial dilator is positioned in the lateral, trans-psoas path, and an elongate penetration wire deliverable to a spinal disc along a lateral, trans-psoas path to the lumbar spine such that a distal tip region of the elongate penetration wire penetrates into an annulus of the spinal disc, wherein the elongate penetration wire is configured to be removably received within the initial dilator; and
- a three-bladed retractor assembly slidable over an outermost dilator of the plurality of sequential dilators toward the spinal disc along the lateral, trans-psoas path, wherein the three-bladed retractor assembly enlarges the distraction corridor and thereby forms an operative corridor along the lateral, trans-psoas path to the lumbar spine, the three-bladed retractor assembly including:
    - a blade holder assembly and first, second, and third retractor blades that extend from the blade holder assembly, the first, second, and third retractor blades each having a concave surface region along an inner facing distal end portion,
    - wherein the three-bladed retractor assembly is adjustable from a first position in which the first, second, and third retractor blades are simultaneously slidable over the outermost dilator of the plurality of sequential dilators to a second position in which each of the second and third retractor blades is moved away from the first retractor blade,
    - wherein the second refractor blade is movable relative to the first blade in response to adjustment of the blade holder assembly,
    - wherein the third retractor blade is movable relative to the first blade in response to adjustment of the blade holder assembly, and
    - an extension member to movably engage with the first retractor blade so that a portion of the extension member extends distally from the first retractor blade; and
- wherein when the three-bladed retractor assembly forms the operative corridor along the lateral, trans-psoas path to the lumbar spine, the operative corridor is dimensioned so as to pass an implant through the operative corridor along the lateral, trans-psoas path to the lumbar spine.

22. The system of claim 21, wherein when the three-bladed retractor assembly forms the operative corridor, the first retractor blade is a posterior-most retractor blade, the second blade is a cephalad-most retractor blade, and the third blade is a caudal-most retractor blade.

23. The system of claim 22, wherein when the three-bladed retractor assembly forms the operative corridor, the cephalad-most retractor blade and the caudal-most retractor blade are moved away from one another and a fourth retractor blade is positioned anterior to the cephalad-most retractor blade and the caudal-most retractor blade.

24. The system of clam 21, wherein the extension member is slidable along an engagement slot defined along an inner face of the first retractor blade.

25. The system of claim 24, wherein the extension member is a posterior shim element to anchor into the spinal disc.

26. The system of claim 24, wherein a distal portion of the extension member has a smallest width at a rounded distal tip.

27. The system of claim 21, wherein when the three-bladed retractor assembly forms the operative corridor along the lateral, trans-psoas path when the three-bladed retractor assembly is adjusted to the second position.

28. The system of claim 21, wherein when the three-bladed retractor assembly is in the first position, each of the first, second, and third retractor blades are in generally abutting relation with the other two of the first, second, and third retractor blades.

29. The system of claim 21, further comprising a fourth retractor blade that couples with the blade holder assembly of the three-bladed retractor assembly, wherein the fourth retractor blade releasably couples with the blade holder assembly so that the fourth retractor blade is an anterior-most retractor blade.

30. The system of claim 21, wherein the elongated penetration wire is advanced together with the initial dilator along the lateral, trans-psoas path to the lumbar spine.

31. The system of claim 21, wherein each dilator of the plurality of sequential dilators comprises a stimulation electrode to deliver electrical stimulation for nerve monitoring.

32. The system of claim 21, further comprising a monitoring system that is configured to deliver an electrical stimulation signal to the stimulation electrode of the initial dilator and monitors electromyographic activity detected by a set of sensor electrodes in leg muscle myotomes associated with nerves in the vicinity of the spinal disc.

33. The system of claim 32, wherein the monitoring system comprises: a display device that is configured to display to a user a numeric stimulation threshold required to obtain the electromyographic activity in at least one of said leg muscle myotomes, a control unit, a patient module configured to connect to the control unit via a data cable, an EMG sensor harness having the set of sensor electrodes configured to connect to the patient module, wherein the control unit is configured to receive signals from the patient module and configured to process EMG responses output from the sensor electrodes to extract characteristic information for each of said leg muscle myotomes.

* * * * *